(12) United States Patent
Shimizu et al.

(10) Patent No.: US 11,548,926 B2
(45) Date of Patent: Jan. 10, 2023

(54) METHOD FOR PRODUCING AN ACTIVE HEPATOCYTE GROWTH FACTOR (HGF)

(71) Applicant: EISAI R&D MANAGEMENT CO., LTD., Tokyo (JP)

(72) Inventors: Masashi Shimizu, Tsukuba (JP); Toshitaka Sato, Kobe (JP); Yoshihisa Arita, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/078,568

(22) PCT Filed: Mar. 15, 2017

(86) PCT No.: PCT/JP2017/010355
§ 371 (c)(1),
(2) Date: Aug. 21, 2018

(87) PCT Pub. No.: WO2017/159722
PCT Pub. Date: Sep. 21, 2017

(65) Prior Publication Data
US 2019/0062390 A1    Feb. 28, 2019

(30) Foreign Application Priority Data
Mar. 17, 2016  (JP) .............................. JP2016-054128

(51) Int. Cl.
| C07K 14/475 | (2006.01) |
| C12P 21/02 | (2006.01) |
| C12N 9/64 | (2006.01) |
| C12N 15/09 | (2006.01) |
| C12N 5/10 | (2006.01) |

(52) U.S. Cl.
CPC ............ *C07K 14/4753* (2013.01); *C12N 9/64* (2013.01); *C12P 21/02* (2013.01); *C12N 5/10* (2013.01); *C12N 15/09* (2013.01)

(58) Field of Classification Search
None
See application file for complete search history.

(56) References Cited

U.S. PATENT DOCUMENTS

| 5,004,805 A | 4/1991 | Gohda et al. | |
| 5,466,593 A * | 11/1995 | Shimomura | C07K 14/475 |
| | | | 435/219 |
| 5,587,359 A | 12/1996 | Higashio et al. | |
| 5,677,164 A * | 10/1997 | Shimomura | C07K 14/475 |
| | | | 435/212 |
| 5,804,557 A | 9/1998 | Cleland et al. | |
| 7,741,096 B2 * | 6/2010 | Eigenbrot, Jr. | C07K 14/4753 |
| | | | 435/212 |
| 2001/0051604 A1 | 12/2001 | Tanaka et al. | |
| 2005/0220758 A1 | 10/2005 | Zobel et al. | |
| 2009/0233863 A1 | 9/2009 | Adachi et al. | |
| 2010/0137213 A1 | 6/2010 | Fernandez et al. | |
| 2013/0071931 A1 | 3/2013 | Ishikawa | |
| 2013/0142792 A1 | 6/2013 | Rothlein et al. | |
| 2014/0234341 A1 | 8/2014 | Tsubouchi et al. | |
| 2017/0189487 A1 | 7/2017 | Ohori et al. | |
| 2020/0341014 A1 | 10/2020 | Kimura et al. | |
| 2022/0267393 A1 | 8/2022 | Shimizu et al. | |

FOREIGN PATENT DOCUMENTS

| AU | 2017232582 | 9/2017 |
| CN | 1367703 A | 9/2002 |
| CN | 102271707 | 12/2011 |
| EP | 0 596 524 A2 * | 5/1994 |
| EP | 1180368 | 2/2002 |
| JP | S63-22526 A | 1/1988 |
| JP | H03-285693 | 12/1991 |
| JP | H04-030000 | 1/1992 |
| JP | H05-103670 | 4/1993 |
| JP | H5-103670 A | 4/1993 |
| JP | H05-111383 | 5/1993 |
| JP | H06-153966 | 6/1994 |
| JP | H6-153966 A | 6/1994 |
| JP | 2577091 B | 1/1997 |
| JP | H09-025241 | 1/1997 |
| JP | 2747979 B | 5/1998 |
| JP | H10-167982 | 6/1998 |

(Continued)

OTHER PUBLICATIONS

Shimomura et al., Cytotechnology, 8:219-229, 1992.*
Gohda et al., "Purification and partial characterization of hepatocyte growth factor from plasma of a patient with fulminant hepatic failure," The Journal of Clinical Investigation, Feb. 1, 1988, 81:414-419.
Kirchhofer et al., "Tissue Expression, Protease Specificity, and Kunitz Domain Functions of Hepatocyte Growth Factor Activator Inhibitor-1B (HAI-1B), a New Splice Variant of HAI-1," The Journal of Biological Chemistry, Jun. 18, 2003, 278(38):36341-36349.
International Search Report in International Application No. PCT/JP2017/010355, dated May 30, 2017, 4 pages (with English Translation).
Nakamura et al., "Hepatocyte growth factor twenty years on: Much more than a growth factor," Journal of Gastroenterology and Hepatology, (2011), 26(S1):188-202.

(Continued)

*Primary Examiner* — Marianne P Allen
(74) *Attorney, Agent, or Firm* — Fish & Richardson P.C.

(57) ABSTRACT

The present invention provides a method for producing active hepatocyte growth factor activator (HGFA) and active hepatocyte growth factor (HGF) without using animal serum. The present invention relates to a method for producing active HGFA without using animal serum. The method is characterized in that it comprises a step of obtaining a culture supernatant comprising pro-HGFA by culturing mammalian cells expressing inactive hepatocyte growth factor activator (pro-HGFA) in a medium without serum, and a step of adjusting the culture supernatant comprising pro-HGFA obtained in the above step to weakly acidic to convert pro-HGFA into active HGFA. The present invention also relates to a method for producing active HGF with HGFA produced by said method.

18 Claims, 5 Drawing Sheets

Specification includes a Sequence Listing.

(56) References Cited

FOREIGN PATENT DOCUMENTS

| | | |
|---|---|---|
| JP | 2859577 B | 2/1999 |
| JP | H11-056382 | 3/1999 |
| JP | 3072628 B | 7/2000 |
| JP | 3213985 B | 10/2001 |
| JP | 2010-513462 | 4/2010 |
| JP | 2012-051822 | 3/2012 |
| JP | 2012-507553 | 3/2012 |
| JP | 2013-520166 | 6/2013 |
| KR | 10-2002-0064141 | 8/2002 |
| RU | 2113480 C | 6/1998 |
| RU | 2316348 | 2/2008 |
| RU | 2506946 C | 2/2014 |
| TW | 201141507 A | 12/2011 |
| WO | WO 1990/010651 | 9/1990 |
| WO | WO 2000/072873 | 12/2000 |
| WO | WO 2006/014928 | 2/2006 |
| WO | WO 2007/122975 | 11/2007 |
| WO | WO 2008/078189 | 7/2008 |
| WO | WO 2008/102849 | 8/2008 |
| WO | WO 2011/049868 | 4/2011 |
| WO | WO 2012/144535 | 10/2012 |
| WO | WO 2014/063128 | 4/2014 |

OTHER PUBLICATIONS

Office Action in Israeli Patent Application No. 261066, dated May 5, 2019, 6 pages (with English Translation).
Response and Amendment filed in Israeli Patent Application No. 261066, dated Aug. 21, 2019, 5 pages (with English Translation).
Supplemental Response and Amendment filed in Israeli Patent Application No. 261066, dated Sep. 3, 2019, 5 pages (with English Translation).
Notice of Allowance in Taiwanese Patent Application No. 104113328, dated Jun. 13, 2019, 5 pages (with English Translation).
Office Action in Australian Patent Application No. 2015254307, dated Jun. 25, 2019, 3 pages.
Amendment and Response filed in Russian Patent Application No. 2016146121, dated Apr. 9, 2019, 11 pages (with English Translation).
Amendment and Response to Japanese Office Action in Japanese Patent Application No. 2016-516354, dated Feb. 7, 2019, 11 pages (with English Translation).
Amendment filed in Japanese Patent Application No. 2016-516354, dated Feb. 7, 2019, 3 pages (with English Translation).
Arshinova et al., "Excipients in technology of lyophilization of drug preparations," Scientific and Manufacturing Journal—Development and Registration of Medicaments, 2013, p. 20-25 (with English Translation).
Chapanian R.et al., "Combined and sequential delivery of bioactive VEGF165 and HGF from poly(trimethylene carbonate) based photo-cross-linked elastomers," Journal of Controlled Release, 2010, vol. 143, p. 53-63.
Decision of Grant for Russian Patent Application No. 2016146121, dated Apr. 25, 2019, 12 pages, (with English Translation).
International Preliminary Report on Patentability in International Application No. PCT/JP2015/062523, dated Nov. 1, 2016, 4 pages.
International Search Report for International Patent Application No. PCT/JP2015/062523 dated Jul. 28, 2015, 6 pages (with English Translation).
International Search Report in International Application No. PCT/JP2017/010587, dated May 23, 2017, 4 pages (with English Translation).
Kaibori et al., "Hepatocyte Growth Factor Stimulates Synthesis of Lipids and Secretion of Lipoproteins in Rat Hepatocytes," Hepatology, (1998), 27(5)1354-1361.
Kosone et al., "HGF ameliorates a high-fat diet-induced fatty liver," American Journal of Physiology-Gastrointestinal and Liver Physiology, (2007), 293(1):G204-G210.

Nakamura et al., "Molecular cloning and expression of human hepatocyte growth factor", Nature, 1989, vol. 342, p. 440-443.
Office Action and Search Report in Chinese Patent Application No. 201580021294.9, dated Mar. 27, 2019, 12 pages (with English Translation).
Office Action in Israeli Patent Application No. 248377, dated Nov. 12, 2018, 6 pages (with English Translation).
Office Action in Japanese Patent Application No. 2016-516354, dated Dec. 11, 2018, 6 pages (with English Translation).
Office Action in Pakistani Patent Application No. 234/2015, dated Oct. 4, 2018, 2 pages.
Office Action in Russian Patent Application No. 2016146121, dated Nov. 28, 2018, 12 pages (with English Translation).
Office Action in Taiwanese Patent Application No. 104113328, dated Jan. 9, 2019, 7 pages (with English Translation).
Office Action issued in Israeli Patent Application No. 248377, dated Jan. 15, 2018, 5 pages (with English translation).
Office Action issued in Pakistan Patent Application No. 234/2015, dated Oct. 6, 2017, 2 pages (English translation).
Ota et al., "Changes in Blood Concentration of Human Hepatocyte Growth Factor (hHGF) and Apolipoprotein A-IV After Transcatheter Arterial Embolization (TAE) in Hepatocyte Cancer Patients," The Japanese Journal of Clinical and Experimental Medicine, (1994), 71(8):245-247 (with English Translation).
Rafferty et al., "International Standards for hepatocyte growth factor/scatter factor: initial assessment of candidate materials and their evaluation by multicentre collaborative study", Journal of Immunological Methods, vol. 258, p. 1-11, 2001.
Response and Amendment filed in Russian Patent Application No. 2016146121, dated Apr. 17, 2019, 8 pages (with English Translation).
Response and Amendment for Pakistani Patent Application No. 234-2015, filed on Nov. 27, 2018, 4 pages.
Response file on Jul. 4, 2018 for the European Patent Application No. 15786509.8, 12 pages.
Response filed in Taiwanese Patent Application No. 104113328, dated Mar. 25, 2019, 13 pages (with English Translation).
Response filed on May 11, 2018 for the Israeli Patent Application No. 248377, 2 pages (with English Translation).
Response to Office Action filed in Pakistani Patent Application No. 234/2015, dated Jan. 11, 2018, 7 pages.
Response to Office Action in Israeli Patent Application No. 248377, dated Feb. 26, 2019, 6 pages (with English Translation).
Search Report in Russian Patent Application No. 2016146121, dated Nov. 26, 2018, 6 pages (with English Translation).
Sino Biological [online], "Human HGF/Hepatocyte Growth Factor Protein," Jun. 2012, [retrieved on Jun. 22, 2017], Retrieved from: URL<http:www.sinobiological.com/HGF-Protein-g-5402.html>, 3 pages.
Sino Biological [online], "Mouse HGF/Hepatocyte Growth Factor Protein," Jun. 2012, [retrieved on Jun. 22, 2017], Retrieved from: URL<http:www.sinobiological.com/HGF-Hepatocyte-Growth-Factor-g-10551.html>, 3 pages.
Stan et al., "Apo A-IV: an update on regulation and physiologic functions," Biochimica et Biophysica Acta, (2003), 1631(2):177-187.
Supplementary European Search Report issued in European Application No. 15786509.8 dated Jan. 3, 2018, 6 pages.
Suzuki, Y. "Production Technology and Quality Problems of Freeze-Dried Parenteral Formulations", Pharm. Tech. Japan, vol. 8, No. 1, p. 75-87, 1992 (with English Translation).
Tahara et al., "Hepatocyte growth factor leads to recovery from alcohol-induced fatty liver in rats," The Journal of Clinical Investigation, (1999), 103(3):313-320.
The Japanese Pharmacopoeia Sixteenth Edition, p. 113-116, 973-974 (Mar. 24, 2011) with English translation.
Written Opinion in International Application No. PCT/JP2015/062523, dated Jul. 28, 2015, 4 pages (English translation).
Xu et al., "Transcriptional regulation of apolipoprotein A-IV by the transcription factor CREBH," Journal of Lipid Research, (2014), 55:850-859.

(56) References Cited

OTHER PUBLICATIONS

Xu et al., "Transforming growth factor-beta down-regulates apolipoprotein M in HepG2 cells," Biochimica et Biophysica Acta, (2004), 1683(1-3):33-37.
Decision of Grant for Japanese Patent Application No. 2016-516354, dated Jul. 24, 2019, 4 pages (with English Translation).
Notice of Allowance in Chinese Patent Application No. 201580021294.9, dated Sep. 19, 2019, 3 pages (with English Translation).
Office Action in Australian Patent Application No. 2015254307, dated Oct. 10, 2019, 3 pages.
Response and Amendment filed in Australian Patent Application No. 2015254307, dated Oct. 10, 2019, 10 pages.
Response filed in Australian Patent Application No. 2015254307, dated Oct. 14, 2019, 4 pages.
Response filed in Chinese Patent Application No. 201580021294.9, dated Aug. 7, 2019, 16 pages (with English Translation).
Telephonic Notice Response filed in Chinese Patent Application No. 201580021294.9, dated Aug. 26, 2019, 12 pages (with English Translation).
European Extended Search Report in European Patent Application No. 17766718.5, dated Oct. 22, 2019, 5 pages.
Response and Amendment filed in European Patent Application No. 17766718.5, dated Nov. 22, 2019, 9 pages.
Notice of Acceptance in Australian Patent Application No. 2015254307, dated Oct. 24, 2019, 3 pages.
Office Action in Indian Patent Application No. 201647036821, dated Nov. 27, 2019, 6 pages.
Office Action in Mexican Patent Application No. MX/a/2016/013667, dated Nov. 5, 2019, 8 pages (with English Translation).
Cell Signaling Technology [Online], "ApoA4 (1D6B6) Mouse mAb," Feb. 2016, [Retrieved on Sep. 10, 2019], retrieved from: URL<https://media.cellsignal.com/pdf/5700.pdf>, 1 page.
European Extended Search Report in European Patent Application No. 17766767.2, dated Sep. 19, 2019, 7 pages.
Response and Amended Claims filed in European Patent Application No. 17766767.2, dated Nov. 19, 2019, 5 pages.
Response filed in Mexican Patent Application No. MX/a/2016/013667, dated Jan. 8, 2020, 10 pages (with English Translation).
Notice of Allowance in Israeli Patent Application No. 248377, dated Jan. 15, 2020, 8 pages (with English Translation).
Notice of Allowance in Mexican Patent Application No. MX/a/2016/013667, dated Feb. 4, 2020, 5 pages (with English Translation).
Notice of Allowance in U.S. Appl. No. 15/305,049, dated Sep. 17, 2019, 14 pages.
Response filed in U.S. Appl. No. 15/305,049, dated Dec. 16, 2019, 2 pages.
Acceptance Fee Receipt in Australian Patent Application No. 2015254307, dated Dec. 9, 2019, 1 page.
Certificate of Patent in Australian Patent No. 2015254307, granted on Feb. 20, 2020, 1 page.
Certificate of Patent in Japanese Patent No. 6568846, granted on Aug. 9, 2019, 2 pages (with English Translation).
Certificate of Patent in Russian Patent No. 2693472, granted on Jul. 3, 2019, 66 pages (with English Translation).
Certificate of Patent in Taiwanese Patent No. I674902, granted on Oct. 21, 2019, 2 pages (with English Translation).
Corrected Notice of Allowability in U.S. Appl. No. 15/305,049, dated Jan. 27, 2020, 7 pages.
Corrected Notice of Allowability in U.S. Appl. No. 15/305,049, dated Mar. 5, 2020, 7 pages.
Notice of Allowance in U.S. Appl. No. 15/305,049, dated Dec. 27, 2018, 10 pages.
Office Action in U.S. Appl. No. 15/305,049, dated Jan. 12, 2018, 8 pages.
Office Action in U.S. Appl. No. 15/305,049, dated Jul. 5, 2017, 12 pages.
Office Action in U.S. Appl. No. 15/305,049, dated Sep. 4, 2018, 13 pages.
Official Receipt Payment of Request for Examination in Australian Patent Application No. 2015254307, dated Mar. 5, 2019, 1 page.
Official Receipt Payment of Request for Examination in Brazilian Patent Application No. BR112016025051-6, dated Mar. 7, 2018, 4 pages (with English Translation).
Request for Continued Examination filed in U.S. Appl. No. 15/305,049, dated Apr. 6, 2018, 15 pages.
Request for Continued Examination filed in U.S. Appl. No. 15/305,049, dated Mar. 25, 2019, 11 pages.
Request for Continued Examination fded in U.S. Appl. No. 15/305,049, dated Apr. 3, 2020, 9 pages.
Request for Continued Examination filed in U.S. Appl. No. 15/305,049, dated Feb. 19, 2020, 8 pages.
Request for Continued Examination fded in U.S. Appl. No. 15/305,049, dated Jan. 16, 2020, 8 pages.
Request for Examination in Canadian Patent Application No. 2947396, dated Feb. 6, 2020, 1 page.
Request for Examination in Chinese Patent Application No. 201580021294.9, filed on Oct. 26, 2016, 2 pages (with English Translation).
Request for Examination in Japanese Patent Application No. 2016-516354, filed on Feb. 29, 2018, 2 pages (with English Translation).
Request for Examination in Korean Patent Application No. 10-2016-7029770, filed on Nov. 18, 2019, 2 pages (with English Translation).
Request for Examination in Russian Patent Application No. 2016146121, dated Apr. 13, 2018, 2 pages (with English Translation).
Request for Examination in Taiwanese Patent Application No. 104113328. dated Mar. 8, 2018, 6 pages (with English Translation).
Request for Examination with the Voluntary Amendment in Singaporean Patent Application No. 10201809228R, filed on Apr. 2, 2020, 10 pages.
Request for Examination, Form 18, in Indian Patent Application No. 201647036821, dated Feb. 23, 2018, 1 page.
Response filed in Indian Patent Application No. 201647036821, dated Apr. 14, 2020, 10 pages.
Response filed in U.S. Appl. No. 15/305,049, dated Nov. 1, 2018, 8 pages.
Response filed in U.S. Appl. No. 15/305,049, dated Oct. 26, 2017, 12 pages.
Technical Report in Brazilian Patent Application No. 112016025051-6, issued on Mar. 5, 2020, 2 pages (with English Translation).
Communication pursuant to Article 94(3) EPC in European Patent Application No. 17766767.2, dated Jun. 23, 2020, 6 pages.
Notice of Allowance in U.S. Appl. No. 15/305,049, dated May 18, 2020, 11 pages.
Response filed in European Patent Application No. 17766767.2, dated Aug. 5, 2020, 7 pages.
Certificate of Patent for Israeli Patent No. 248377, granted on Jul. 31, 2020, 2 pages.
Office Action in Israeli Patent Application No. 261066, dated Jul. 30, 2020, 3 pages.
Preliminary Office Action with Technical Report in Brazilian Patent Application No. BR112016025051-6, dated Jun. 16, 2020, 8 pages (with English Translation).
Request for Continued Examination filed in U.S. Appl. No. 15/305,049, filed Aug. 13, 2020, 3 pages.
Response and Amendment filed in Israeli Patent Application No. 261066, dated Aug. 27, 2020, 6 pages.
Response to Restriction Requirement filed in U.S. Appl. No. 16/078,557, filed Sep. 28, 2020, 3 pages.
Restriction Requirement in U.S. Appl. No. 16/078,557, dated Aug. 26, 2020, 8 pages.
Apalikova et al., "Sorbing Polymers Based on Iron Oxyhydrates," Bulletin of Chelyabinsk Scientific Center, South Ural State University, Chelyabinsk, Russia, Aug. 2000, vol. 3, UDC:546.723-36 (with English Translation).
Communication under Rule 71(3) EPC in European Patent Application No. 15786509.8, dated Feb. 16, 2021, 69 pages.
Hüpeden et al., "Relative abundance of *Nitrotoga* spp. in a biofilter of a cold-freshwater aquaculture plant appears to be stimulated by slightly acidic pH," Applied and Environmental Microbiology, Mar. 2016, 82(6): 1838-1845.

(56) References Cited

OTHER PUBLICATIONS

Kamimoto et al., "Hepatocyte growth factor prevents multiple organ injuries in endotoxemic mice through a heme oxygenase-1-dependent mechanism," Biochemical and Biophysical Research Communications, 2009, 380:333-337.
Kataoka et al., "Hepatocyte growth factor activator (HGFA): pathophysiological functions in vivo," MiniReview, The FEBS Journal, 2010, 277(10):2230-2237.
Mukai et al., "Activation of hepatocyte growth factor activator zymogen (pro-HGFA) by human kallikrein 1-related peptidases," The FEBS Journal, 2008, 275:1003-1017.
Notice of Allowance in United States U.S. Appl. No. 15/305,049, dated Oct. 14, 2020, 9 pages.
Office Action in Canadian Patent Application No. 2947396, dated Dec. 23, 2020, 4 pages.
Office Action in Indian Patent Application No. 201847031049, dated Oct. 19, 2020, 6 pages.
Office Action in Israeli Patent Application No. 261066, dated Jul. 30, 2020, 6 pages (with English Translation).
Office Action in Japanese Patent Application No. 2018-505994, dated Aug. 3, 2020, 8 pages (with English Translation).
Office Action in Japanese Patent Application No. 2018-505994, dated Oct. 5, 2020, 6 pages (with English Translation).
Office Action in Japanese Patent Application No. 2018-505972, dated Sep. 23, 2020, 10 pages (with English Translation).
Office Action in Korean Patent Application No. 10-2018-7024470, dated Dec. 21, 2020, 5 pages (with English Translation).
Office Action in Pakistani Patent Application No. 234/2015, dated Jan. 18, 2021, 2 pages.
Office Action in Russian Patent Application No. 2018130530, dated Aug. 13, 2020, 16 pages (with English Translation).
Office Action in Russian Patent Application No. 2018130530, dated Dec. 16, 2020, 6 pages (with English Translation).
Office Action in U.S. Appl. No. 16/078,557, dated Nov. 17, 2020, 37 pages.
Parr et al., "Expression of hepatocyte growth factor/scatter factor, its activator, inhibitors and the c-Met receptor in human cancer cells," International Journal of Oncology, Oct. 200, 19:857-863.
Request for Continued Examination filed in U.S. Appl. No. 15/305,049, dated Jan. 7, 2021, 5 pages.
Response and Claim Amendment filed in Russian Patent Application No. 2018130530, dated Nov. 12, 2020, 10 pages (with English Translation).
Response and Claim Amendment filed in Russian Patent Application No. 2018130530, dated Feb. 8, 2021, 6 pages (with English Translation).
Response filed in Indian Patent Application No. 201847031049, dated Feb. 15, 2021, 8 pages.
Response filed in Korean Patent Application No. 10-2018-7024470, dated Feb. 9, 2021, 19 pages (with English Translation).
Response filed in U.S. Appl. No. 16/078,557, dated Feb. 17, 2021, 9 pages.
Response to the Preliminary Office Action in Brazilian Patent Application No. BR112016025051-6, dated Sep. 8, 2020, to the Preliminary Office Action dated Jun. 16, 2020, 24 pages (with English Translation).
Selvarasu et al., "Combined In Silico Modeling and Metabolomics Analysis to Characterize Fed-Batch CHO Cell Culture," Biotechnology and Bioengineering, Jun. 2012, 109(6): 1415-1429.
Suzuki et al., "Skeletal Muscle Injury Induces Hepatocyte Growth Factor Expression in Spleen," Biochemical and Biophysical Research Communications, 2002, 292:709-714.
Written Argument and Amendment Response in Japanese Patent Application No. 2018-505994, dated Aug. 25, 2020, 11 pages (with English Translation).
Written Argument and Amendment Response in Japanese Patent Application No. 2018-505994, dated Oct. 26, 2020, 6 pages (with English Translation).
Written Argument and Amendment Response in Japanese Patent Application No. 2018-505972, dated Oct. 26, 2020, 9 pages (with English Translation).
Office Action in Korean Patent Application No. 10-2016-7029770, dated Feb. 26, 2021, 7 pages (with English Translation).
Notice of Allowance in Japanese Patent Application No. 2018-505972, dated Mar. 22, 2021, 6 pages (with English Translation).
Communication under Rule 71(3) EPC in European Patent Application No. 17766718.5, dated Apr. 28, 2021, 51 pages.
Decision of Grant for Russian Patent Application No. 2018130530, dated Apr. 7, 2021, 14 pages (with English Translation).
Letter Patent granted in Mexican Patent No. 372156, dated Mar. 11, 2021, 106 pages (with English Translation).
Notice of Allowance in Taiwanese Patent Application No. 108125333, dated Mar. 11, 2021, 7 pages (with English Translation).
Notice of Allowance in U.S. Appl. No. 15/305,049, dated Apr. 30, 2021, 7 pages.
Office Action in U.S. Appl. No. 15/305,049, dated Mar. 16, 2021, 5 pages.
Office Action in U.S. Appl. No. 16/078,557, dated May 12, 2021, 10 pages.
Response and Amendment filed in Korean Patent Application No. 10-2016-7029770, dated Apr. 22, 2021, 17 pages (with English Translation).
Response filed in Canadian Patent Application No. 2,947,396, dated Apr. 8, 2021, 8 pages.
Response filed in U.S. Appl. No. 15/305,049, dated Apr. 9, 2021, 5 pages.
Voluntary Amendment filed in Taiwanese Patent Application No. 108125333, dated Jan. 15, 2020, 14 pages (with English Translation).
IN Official Communication of the Intimation of Grant and Patent Certificate of Indian Patent No. 371199 in Indian Appln. No. 201647036821, dated Jul. 6, 2021, 2 pages (with English Translation).
Request for Continued Examination filed in U.S. Appl. No. 15/305,049, dated May 20, 2021, 5 pages.
Communication pursuant to Article 94(3) EPC in European Patent Application No. 17766767.2, dated Apr. 6, 2021, 5 pages.
Letter Patent granted in Korean Patent No. 10-2291913, dated Aug. 13, 2021, 3 pages (with English Translation).
Office Action and Search Report in Chinese Patent Application No. 201780013057.7, dated Aug. 10, 2021, 15 pages (with English Translation).
Request for Continued Examination filed in U.S. Appl. No. 15/305,049, filed Aug. 25, 2021, 5 pages.
Response and Amendment filed in European Patent Application No. 17766767.2, dated Jul. 19, 2021, 19 pages.
Notice of Eligibility for Grant and Supplementary Examination Report in Singaporean Patent Application No. 10201809228R, dated Sep. 7, 2021, 4 pages.
Letter Patent granted in European Patent No. 3138575, dated Jul. 14, 2021, 2 pages.
Letter Patent granted in Taiwanese Patent No. 1728409, dated May 21, 2021, 2 pages (with English Translation).
Notice of Allowance in Canadian Patent Application No. 2947396, dated Jul. 23, 2021, 1 page (with English Translation).
Notice of Allowance in Israeli Patent Application No. 261066, dated Jun. 7, 2021, 7 pages (with English Translation).
Notice of Allowance in Korean Patent Application No. 10-2016-7029770, dated Jul. 28, 2021, 3 pages (with English Translation).
Notice of Allowance in U.S. Appl. No. 15/305,049, dated Jul. 27, 2021, 12 pages.
Request for Examination in Russian Patent Application No. 2019119586, dated Jul. 29, 2021, 2 pages (with English Translation).
Certificate of Patent and Notification of Grant in Singaporean Patent Application No. 10201809228R, dated Oct. 8, 2021, 3 pages.
Letter Patent granted in Canadian Patent No. 2947396, dated Oct. 19, 2021, 61 pages.
Response and Claim Amendment filed in Chinese Patent Application No. 201780013057.7, dated Oct. 26, 2021, 10 pages (English Translation only).

(56) References Cited

OTHER PUBLICATIONS

Certificate of Patent in Chinese Patent No. ZL 2017800130577, announced on Jan. 11, 2022, 4 pages (with English Translation).
Certificate of Patent in Israeli Patent No. 261066, granted on Dec. 1, 2021, 2 pages (with English Translation).
Notice of Eligibility for Grant and Support Therefor in Singaporean Patent Application No. 11201806843U, dated Jan. 12, 2022, 4 pages.
Notice to Grant a Patent for Invention in Chinese Patent Application No. 201780013057.7, dated Dec. 17, 2021, 2 pages (with English Translation).
Notification of Patent Registration in Chinese Patent Application No. 201780013057.7, dated Dec. 17, 2021, 2 pages (with English Translation).
Office Action in Russian Patent Application No. 2019119586, dated Jan. 25, 2022 9 pages (with English Translation).
Search Report in Russian Patent Application No. 2019119586, dated Jan. 24, 2022, 4 pages (with English Translation).
Certificate of Patent in Singaporean Patent No. 11201806843U, granted on Apr. 13, 2022, 1 page.
Notification of Grant in Singaporean Patent Application No. 11201806843U, dated Apr. 13, 2022, 2 pages.
Response filed in Russian Patent Application No. 2019119586, dated Apr. 29, 2022, 9 pages (with English Translation).
Office Action in Australian Patent Application No. 2017232582, dated May 30, 2022, 3 pages.
Response filed in Australian Patent Application No. 2017232582, dated Jun. 20, 2022, 17 pages.
Notice of Acceptance in Australian Patent Application No. 2017232582, dated Jun. 29, 2022, 3 pages.
Decision of Grant for Russian Patent Application No. 2019119586, dated Jun. 22, 2022, 15 pages (with English Translation).
Office Action in Mexican Patent Application No. MX/a/2018/010283, dated May 24, 2022, 8 pages (with English Translation).
Response filed in Mexican Patent Application No. MX/a/2018/010283, dated Jul. 1, 2022, 17 pages (with English Translation).
Notice of Allowance in Mexican Patent Application No. MX/a/2018/010283, dated Jul. 5, 2022, 4 pages (with English Translation).
Letter Patent granted in Mexican Patent No. 395311, dated Sep. 5, 2022, 60 pages (with Cover Page Translation).
Letter Patent granted in Russian Patent No. 2776108, dated Jul. 13, 2022, 5 pages, (with Cover Page Translation).
Letter Patent granted in Australian Patent No. 2017232582, dated Oct. 27, 2022, 1 page.

\* cited by examiner

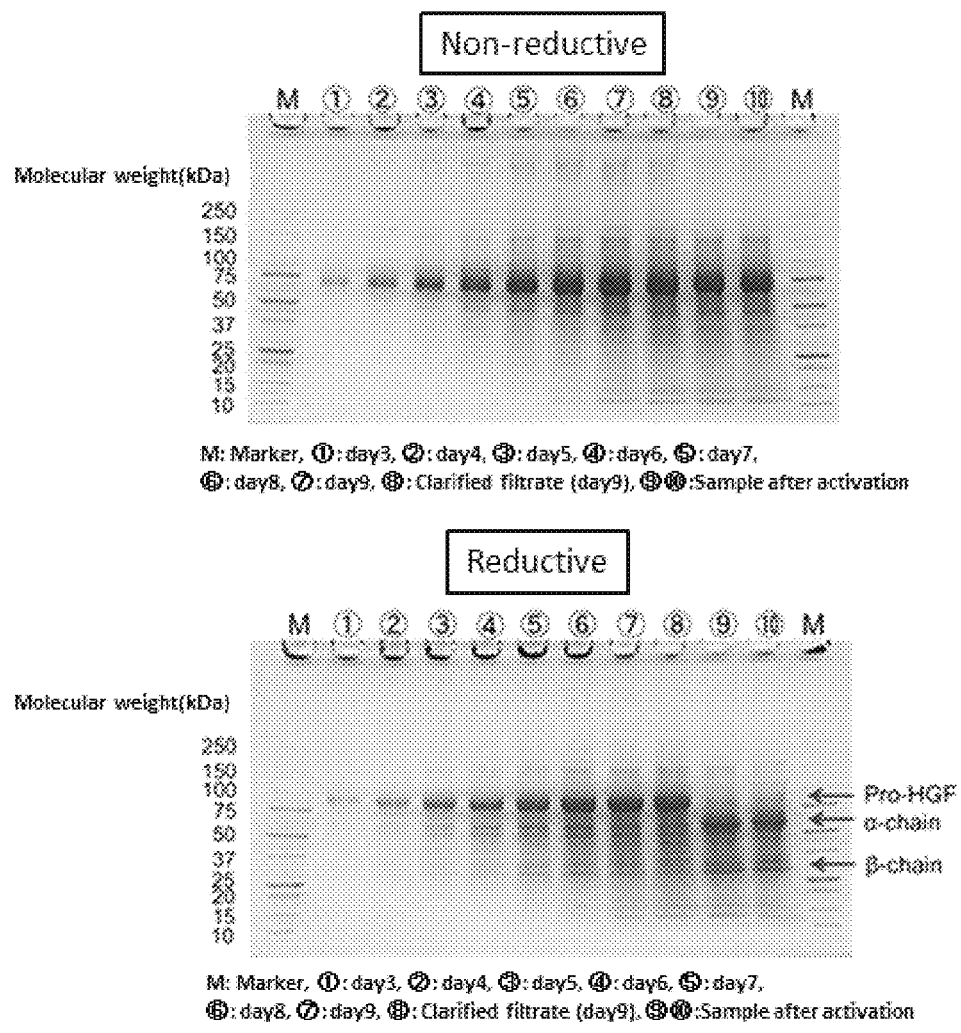
Figure 1  Confirmation of Pro-HGF Activation by SDS-PAGE

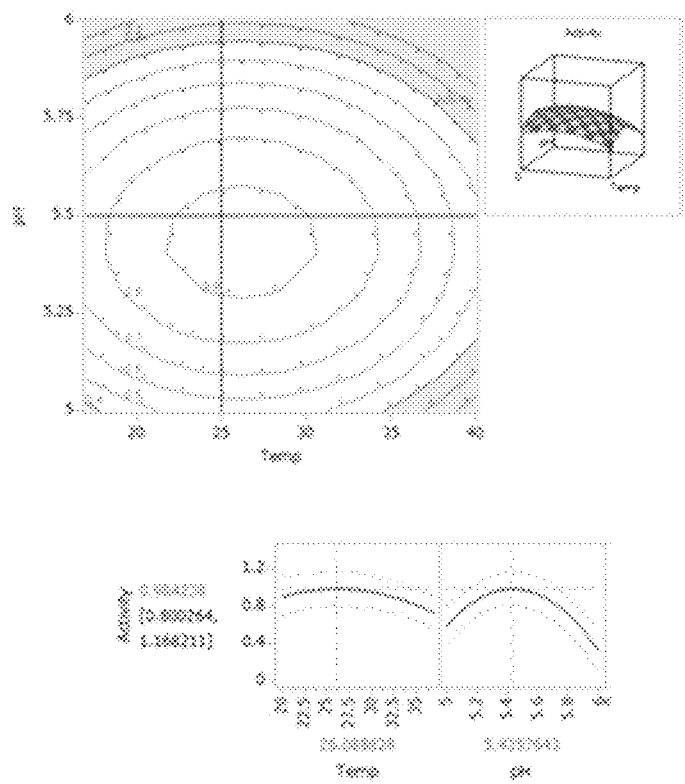
Figure 2    Optimization Profile of HGFA Activation Condition Employing Central Composite Design
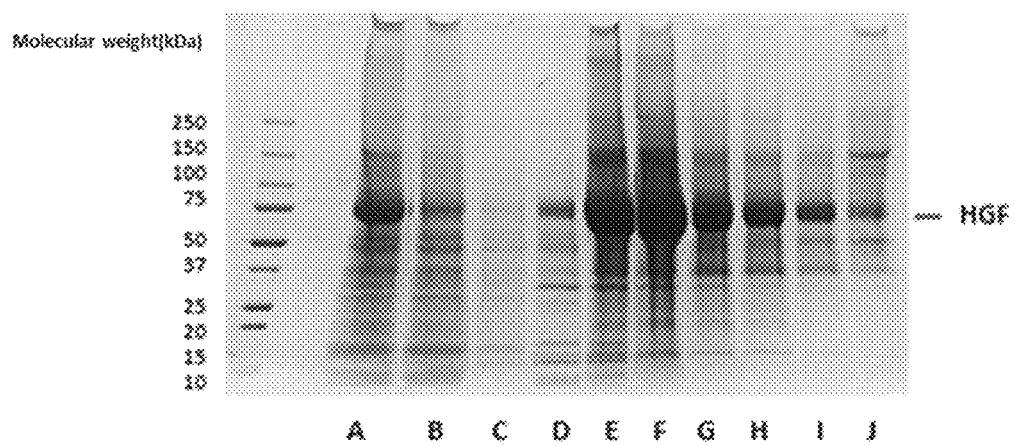
A: Column loading solution B: Flow-through C: Wash D: 0.25M
E: 0.7M 1CV F: 0.7M 2CV G: 0.7M 3CV H: 0.7M 4CV
I: 0.7M 5CV J: 1M 2CV pool  Concentration means arginine concentration
Figure 3

M: Molecular weight marker, B: Blank
①⑦⑤ HGF purified product, ③④⑨⑩ pro-HGF purified product,
⑤⑧⑪⑫ HGF purified product (with unconverted)

Figure 5: SDS-PAGE of Purified Pro-HGF Product

SEQUENCE LISTING

<160> NUMBER OF SEQ ID NOS: 2

<210> SEQ ID NO 1
<211> LENGTH: 697

```
<212> TYPE: PRT
<213> ORGANISM: Homo sapiens

<400> SEQUENCE: 1
```

| | | | | | | | | | | | | | | |
|---|---|---|---|---|---|---|---|---|---|---|---|---|---|---|
| Gln | Arg | Lys | Arg | Arg | Asn | Thr | Ile | His | Glu | Phe | Lys | Lys | Ser | Ala | Lys |
| 1 | | | | 5 | | | | | 10 | | | | | 15 | |
| Thr | Thr | Leu | Ile | Lys | Ile | Asp | Pro | Ala | Leu | Lys | Ile | Lys | Thr | Lys | Lys |
| | | | 20 | | | | | 25 | | | | | 30 | | |
| Val | Asn | Thr | Ala | Asp | Gln | Cys | Ala | Asn | Arg | Cys | Thr | Arg | Asn | Lys | Gly |
| | | 35 | | | | | 40 | | | | | 45 | | | |
| Leu | Pro | Phe | Thr | Cys | Lys | Ala | Phe | Val | Phe | Asp | Lys | Ala | Arg | Lys | Gln |
| | 50 | | | | | 55 | | | | | 60 | | | | |
| Cys | Leu | Trp | Phe | Pro | Phe | Asn | Ser | Met | Ser | Ser | Gly | Val | Lys | Lys | Glu |
| 65 | | | | | 70 | | | | | 75 | | | | | 80 |
| Phe | Gly | His | Glu | Phe | Asp | Leu | Tyr | Glu | Asn | Lys | Asp | Tyr | Ile | Arg | Asn |
| | | | | 85 | | | | | 90 | | | | | 95 | |
| Cys | Ile | Ile | Gly | Lys | Gly | Arg | Ser | Tyr | Lys | Gly | Thr | Val | Ser | Ile | Thr |
| | | | 100 | | | | | 105 | | | | | 110 | | |
| Lys | Ser | Gly | Ile | Lys | Cys | Gln | Pro | Trp | Ser | Ser | Met | Ile | Pro | His | Glu |
| | | 115 | | | | | 120 | | | | | 125 | | | |
| His | Ser | Phe | Leu | Pro | Ser | Ser | Tyr | Arg | Gly | Lys | Asp | Leu | Gln | Glu | Asn |
| | 130 | | | | | 135 | | | | | 140 | | | | |
| Tyr | Cys | Arg | Asn | Pro | Arg | Gly | Glu | Glu | Gly | Gly | Pro | Trp | Cys | Phe | Thr |
| 145 | | | | | 150 | | | | | 155 | | | | | 160 |
| Ser | Asn | Pro | Glu | Val | Arg | Tyr | Glu | Val | Cys | Asp | Ile | Pro | Gln | Cys | Ser |
| | | | | 165 | | | | | 170 | | | | | 175 | |
| Glu | Val | Glu | Cys | Met | Thr | Cys | Asn | Gly | Glu | Ser | Tyr | Arg | Gly | Leu | Met |
| | | | 180 | | | | | 185 | | | | | 190 | | |
| Asp | His | Thr | Glu | Ser | Gly | Lys | Ile | Cys | Gln | Arg | Trp | Asp | His | Gln | Thr |
| | | 195 | | | | | 200 | | | | | 205 | | | |
| Pro | His | Arg | His | Lys | Phe | Leu | Pro | Glu | Arg | Tyr | Pro | Asp | Lys | Gly | Phe |
| | 210 | | | | | 215 | | | | | 220 | | | | |
| Asp | Asp | Asn | Tyr | Cys | Arg | Asn | Pro | Asp | Gly | Gln | Pro | Arg | Pro | Trp | Cys |
| 225 | | | | | 230 | | | | | 235 | | | | | 240 |
| Tyr | Thr | Leu | Asp | Pro | His | Thr | Arg | Trp | Glu | Tyr | Cys | Ala | Ile | Lys | Thr |
| | | | | 245 | | | | | 250 | | | | | 255 | |
| Cys | Ala | Asp | Asn | Thr | Met | Asn | Asp | Thr | Asp | Val | Pro | Leu | Glu | Thr | Thr |
| | | | 260 | | | | | 265 | | | | | 270 | | |
| Glu | Cys | Ile | Gln | Gly | Gln | Gly | Glu | Gly | Tyr | Arg | Gly | Thr | Val | Asn | Thr |
| | | 275 | | | | | 280 | | | | | 285 | | | |
| Ile | Trp | Asn | Gly | Ile | Pro | Cys | Gln | Arg | Trp | Asp | Ser | Gln | Tyr | Pro | His |
| | 290 | | | | | 295 | | | | | 300 | | | | |
| Glu | His | Asp | Met | Thr | Pro | Glu | Asn | Phe | Lys | Cys | Lys | Asp | Leu | Arg | Glu |
| 305 | | | | | 310 | | | | | 315 | | | | | 320 |
| Asn | Tyr | Cys | Arg | Asn | Pro | Asp | Gly | Ser | Glu | Ser | Pro | Trp | Cys | Phe | Thr |
| | | | | 325 | | | | | 330 | | | | | 335 | |
| Thr | Asp | Pro | Asn | Ile | Arg | Val | Gly | Tyr | Cys | Ser | Gln | Ile | Pro | Asn | Cys |
| | | | 340 | | | | | 345 | | | | | 350 | | |
| Asp | Met | Ser | His | Gly | Gln | Asp | Cys | Tyr | Arg | Gly | Asn | Gly | Lys | Asn | Tyr |
| | | 355 | | | | | 360 | | | | | 365 | | | |
| Met | Gly | Asn | Leu | Ser | Gln | Thr | Arg | Ser | Gly | Leu | Thr | Cys | Ser | Met | Trp |
| | 370 | | | | | 375 | | | | | 380 | | | | |
| Asp | Lys | Asn | Met | Glu | Asp | Leu | His | Arg | His | Ile | Phe | Trp | Glu | Pro | Asp |
| 385 | | | | | 390 | | | | | 395 | | | | | 400 |

```
Ala Ser Lys Leu Asn Glu Asn Tyr Cys Arg Asn Pro Asp Asp Ala
            405                 410                 415

His Gly Pro Trp Cys Tyr Thr Gly Asn Pro Leu Ile Pro Trp Asp Tyr
        420                 425                 430

Cys Pro Ile Ser Arg Cys Glu Gly Asp Thr Thr Pro Thr Ile Val Asn
            435                 440                 445

Leu Asp His Pro Val Ile Ser Cys Ala Lys Thr Lys Gln Leu Arg Val
        450                 455                 460

Val Asn Gly Ile Pro Thr Arg Thr Asn Ile Gly Trp Met Val Ser Leu
465                 470                 475                 480

Arg Tyr Arg Asn Lys His Ile Cys Gly Gly Ser Leu Ile Lys Glu Ser
            485                 490                 495

Trp Val Leu Thr Ala Arg Gln Cys Phe Pro Ser Arg Asp Leu Lys Asp
        500                 505                 510

Tyr Glu Ala Trp Leu Gly Ile His Asp Val His Gly Arg Gly Asp Glu
        515                 520                 525

Lys Cys Lys Gln Val Leu Asn Val Ser Gln Leu Val Tyr Gly Pro Glu
    530                 535                 540

Gly Ser Asp Leu Val Leu Met Lys Leu Ala Arg Pro Ala Val Leu Asp
545                 550                 555                 560

Asp Phe Val Ser Thr Ile Asp Leu Pro Asn Tyr Gly Cys Thr Ile Pro
            565                 570                 575

Glu Lys Thr Ser Cys Ser Val Tyr Gly Trp Gly Tyr Thr Gly Leu Ile
        580                 585                 590

Asn Tyr Asp Gly Leu Leu Arg Val Ala His Leu Tyr Ile Met Gly Asn
        595                 600                 605

Glu Lys Cys Ser Gln His His Arg Gly Lys Val Thr Leu Asn Glu Ser
    610                 615                 620

Glu Ile Cys Ala Gly Ala Glu Lys Ile Gly Ser Gly Pro Cys Glu Gly
625                 630                 635                 640

Asp Tyr Gly Gly Pro Leu Val Cys Glu Gln His Lys Met Arg Met Val
            645                 650                 655

Leu Gly Val Ile Val Pro Gly Arg Gly Cys Ala Ile Pro Asn Arg Pro
        660                 665                 670

Gly Ile Phe Val Arg Val Ala Tyr Tyr Ala Lys Trp Ile His Lys Ile
        675                 680                 685

Ile Leu Thr Tyr Lys Val Pro Gln Ser
        690                 695

<210> SEQ ID NO 2
<211> LENGTH: 620
<212> TYPE: PRT
<213> ORGANISM: Homo sapiens

<400> SEQUENCE: 2

Gln Pro Gly Gly Asn Arg Thr Glu Ser Pro Glu Pro Asn Ala Thr Ala
1               5                   10                  15

Thr Pro Ala Ile Pro Thr Ile Leu Val Thr Ser Val Thr Ser Glu Thr
            20                  25                  30

Pro Ala Thr Ser Ala Pro Glu Ala Glu Gly Pro Gln Ser Gly Gly Leu
        35                  40                  45

Pro Pro Pro Pro Arg Ala Val Pro Ser Ser Ser Pro Gln Ala Gln
    50                  55                  60

Ala Leu Thr Glu Asp Gly Arg Pro Cys Arg Phe Pro Phe Arg Tyr Gly
```

-continued

```
               65                  70                  75                  80
         Gly Arg Met Leu His Ala Cys Thr Ser Glu Gly Ser Ala His Arg Lys
                             85                  90                  95

Trp Cys Ala Thr Thr His Asn Tyr Asp Arg Asp Arg Ala Trp Gly Tyr
                            100                 105                 110

Cys Val Glu Ala Thr Pro Pro Gly Gly Pro Ala Ala Leu Asp Pro
                        115                 120                 125

Cys Ala Ser Gly Pro Cys Leu Asn Gly Gly Ser Cys Ser Asn Thr Gln
                        130                 135                 140

Asp Pro Gln Ser Tyr His Cys Ser Cys Pro Arg Ala Phe Thr Gly Lys
         145                 150                 155                 160

Asp Cys Gly Thr Glu Lys Cys Phe Asp Glu Thr Arg Tyr Glu Tyr Leu
                            165                 170                 175

Glu Gly Gly Asp Arg Trp Ala Arg Val Arg Gln Gly His Val Glu Gln
                        180                 185                 190

Cys Glu Cys Phe Gly Gly Arg Thr Trp Cys Glu Gly Thr Arg His Thr
                        195                 200                 205

Ala Cys Leu Ser Ser Pro Cys Leu Asn Gly Gly Thr Cys His Leu Ile
                    210                 215                 220

Val Ala Thr Gly Thr Thr Val Cys Ala Cys Pro Pro Gly Phe Ala Gly
         225                 230                 235                 240

Arg Leu Cys Asn Ile Glu Pro Asp Glu Arg Cys Phe Leu Gly Asn Gly
                            245                 250                 255

Thr Gly Tyr Arg Gly Val Ala Ser Thr Ser Ala Ser Gly Leu Ser Cys
                        260                 265                 270

Leu Ala Trp Asn Ser Asp Leu Leu Tyr Gln Glu Leu His Val Asp Ser
                    275                 280                 285

Val Gly Ala Ala Ala Leu Leu Gly Leu Gly Pro His Ala Tyr Cys Arg
                290                 295                 300

Asn Pro Asp Asn Asp Glu Arg Pro Trp Cys Tyr Val Val Lys Asp Ser
         305                 310                 315                 320

Ala Leu Ser Trp Glu Tyr Cys Arg Leu Glu Ala Cys Glu Ser Leu Thr
                            325                 330                 335

Arg Val Gln Leu Ser Pro Asp Leu Leu Ala Thr Leu Pro Glu Pro Ala
                        340                 345                 350

Ser Pro Gly Arg Gln Ala Cys Gly Arg Arg His Lys Lys Arg Thr Phe
                    355                 360                 365

Leu Arg Pro Arg Ile Ile Gly Gly Ser Ser Ser Leu Pro Gly Ser His
                370                 375                 380

Pro Trp Leu Ala Ala Ile Tyr Ile Gly Asp Ser Phe Cys Ala Gly Ser
         385                 390                 395                 400

Leu Val His Thr Cys Trp Val Val Ser Ala Ala His Cys Phe Ser His
                            405                 410                 415

Ser Pro Pro Arg Asp Ser Val Ser Val Val Leu Gly Gln His Phe Phe
                        420                 425                 430

Asn Arg Thr Thr Asp Val Thr Gln Thr Phe Gly Ile Glu Lys Tyr Ile
                    435                 440                 445

Pro Tyr Thr Leu Tyr Ser Val Phe Asn Pro Ser Asp His Asp Leu Val
                450                 455                 460

Leu Ile Arg Leu Lys Lys Lys Gly Asp Arg Cys Ala Thr Arg Ser Gln
         465                 470                 475                 480

Phe Val Gln Pro Ile Cys Leu Pro Glu Pro Gly Ser Thr Phe Pro Ala
                            485                 490                 495
```

```
Gly His Lys Cys Gln Ile Ala Gly Trp Gly His Leu Asp Glu Asn Val
            500                 505                 510

Ser Gly Tyr Ser Ser Ser Leu Arg Glu Ala Leu Val Pro Leu Val Ala
        515                 520                 525

Asp His Lys Cys Ser Ser Pro Glu Val Tyr Gly Ala Asp Ile Ser Pro
    530                 535                 540

Asn Met Leu Cys Ala Gly Tyr Phe Asp Cys Lys Ser Asp Ala Cys Gln
545                 550                 555                 560

Gly Asp Ser Gly Gly Pro Leu Ala Cys Glu Lys Asn Gly Val Ala Tyr
                565                 570                 575

Leu Tyr Gly Ile Ile Ser Trp Gly Asp Gly Cys Gly Arg Leu His Lys
            580                 585                 590

Pro Gly Val Tyr Thr Arg Val Ala Asn Tyr Val Asp Trp Ile Asn Asp
        595                 600                 605

Arg Ile Arg Pro Pro Arg Arg Leu Val Ala Pro Ser
610                 615                 620
```

METHOD FOR PRODUCING AN ACTIVE HEPATOCYTE GROWTH FACTOR (HGF)

TECHNICAL FIELD

The present invention relates to a method for producing active hepatocyte growth factor activator (also referred to herein as "active HGFA") and active hepatocyte growth factor (also referred to herein as "active HGF") without using animal serum.

SEQUENCE LISTING

This application contains a Sequence Listing that has been submitted electronically as an ASCII text file named SEQLIST1.txt. The ASCII text file, created on Mar. 9, 2017, is 11,671 bytes in size. The material in the ASCII text file is hereby incorporated by reference in its entirety.

BACKGROUND ART

HGF is a factor having hepatic parenchymal cell proliferation activity that is purified from the blood plasma of human fulminant hepatitis patients (Patent Literature 1 and Non-Patent Literature 1), and has been reported as having various pharmacological effects such as antitumoral effect, enhancement of cell-mediated immunity, wound therapeutic effect, and tissue regeneration promotional effect (Patent Literature 2).

Until now, the gene encoding the aforementioned HGF has been cloned and produced by recombinant DNA technology (Patent Literatures 3-5). Moreover, it is known that HGF takes single-stranded and double-stranded forms which are composed of 2 types of subunits (a chain of approximately 60 kDa and β chain of approximately 30 kDa), where the single-stranded form does not have bioactivity and gains bioactivity in the double-stranded form. Further, it is known that in the production by recombinant DNA technology, HGF can be obtained as the active double-stranded form under culturing with animal serum, but under culturing without animal serum, the majority of the HGF produced is obtained as the inactive single-stranded form (e.g. Patent Literature 6). Since a protease contained in animal serum is involved in the conversion from the single-stranded inactive hepatocyte growth factor form (also referred to herein as "pro-HGF") into the double-stranded active HGF form, it is thought necessary to use animal serum in order to efficiently obtain active HGF.

On the other hand, in recent years, the mainstream in the production of biological material by recombinant DNA technology is culturing without animal serum in order to avoid the risk of virus contamination etc. Accordingly, in order to manufacture active HGF with a medium without animal serum, it is necessary to convert the single-stranded pro-HGF form into active HGF by some means. HGFA that can convert pro-HGF into active HGF (Patent Literature 7), or serine protease such as urokinase plasminogen activator (Non-Patent Literature 2) are known as such means. However, there are problems that these enzymes that can convert pro-HGF into active HGF are serum-derived, and when they are required to produce by integration of the gene into microorganisms or animal cells for production, they are produced as the precursor forms in a serum-free culture and therefore difficult to use as they are.

CITATION LIST

Patent Literatures

[Patent Literature 1] Japanese Published Unexamined Patent Application Publication No. S63-22526
[Patent Literature 2] Japanese Patent No. 2747979
[Patent Literature 3] Japanese Patent No. 2577091
[Patent Literature 4] Japanese Patent No. 2859577
[Patent Literature 5] Japanese Patent No. 3072628
[Patent Literature 6] Japanese Patent No. 3213985
[Patent Literature 7] Japanese Published Unexamined Patent Application Publication No. H5-103670

Non-Patent Literatures

[Non-Patent Literature 1] J. Clin. Invest., 81, 414(1988)
[Non-Patent Literature 2] JGH 26 (2011) Suppl. 1; 188-202, p. 192

SUMMARY OF THE INVENTION

Problems to be Solved by the Invention

The object of the present invention is to provide a method for producing active HGFA and active HGF without using animal serum.

The another object of the present invention is to provide active HGFA, active HGF, and preparations thereof produced by the method of the present invention.

Means for Solving the Problems

As a result of extensive investigation by the present inventors to solve the above problems, it was found that by culturing mammalian cells expressing inactive hepatocyte growth factor activator (pro-HGFA) in a medium without serum to obtain the culture supernatant thereof, and subjecting the aforementioned culture supernatant to a particular treatment, pro-HGFA contained in the aforementioned culture supernatant can be converted into active HGFA. Accordingly, since pro-HGF produced under culturing without animal serum can be converted into active HGF by active HGFA similarly produced under culturing without animal serum, active HGF that does not contain animal serum-derived component or a preparation comprising the same can be produced.

Accordingly, the present invention encompasses the following aspects:

[1] A method for producing active hepatocyte growth factor activator (HGFA), characterized in that it comprises:
Step 1:
a step of obtaining a culture supernatant comprising pro-HGFA by culturing mammalian cells expressing inactive hepatocyte growth factor activator (pro-HGFA) in a medium without serum, and
Step 2:
a step of adjusting the culture supernatant comprising pro-HGFA obtained in the above step to weakly acidic to convert pro-HGFA into active HGFA.

[2] The production method according to [1], characterized in that said step further comprises adding sulfated polysaccharides to said culture supernatant.

[3] The production method according to [1] or [2], characterized in that said step of adjusting the culture supernatant to weakly acidic is a step of adjusting pH to 4.0-6.0.

[4] The production method according to any of [1] to [3], characterized in that said step of adjusting the culture supernatant to weakly acidic is performed at a temperature of 15-40° C.

[5] The production method according to any of [1] to [4], characterized in that said culture supernatant is obtained after a decline in the survival rate of mammalian cells in culture.

[6] The production method according to any of [1] to [5], characterized in that said mammalian cell is a Chinese hamster ovary (CHO) cell.

[7] The production method according to any of [1] to [6], characterized in that said pro-HGFA has the amino acid sequence shown in SEQ ID NO. 2.

[8] The production method according to any of [1] to [7], characterized in that said culture supernatant is said culture supernatant per se, a dilution of said culture supernatant, a concentrate of said culture supernatant, or a partially purified product of said culture supernatant.

[9] Active HGFA characterized in that it is obtained by the production method according to any of [1] to [8].

[10] A method for production active hepatocyte growth factor (HGF), characterized in that it comprises a step of allowing active HGFA to act on a culture supernatant comprising inactive hepatocyte growth factor (pro-HGF) to convert said pro-HGF into active HGF, wherein
said culture supernatant comprising pro-HGF is a culture supernatant obtained by culturing cells expressing pro-HGF in a medium without serum, and
said active HGFA is produced by the method according to any of [1] to [8].

[11] The production method according to [10], characterized in that said medium for culturing cells expressing pro-HGF is a medium without any animal-derived components.

[12] The production method according to [10] or [11], characterized in that said pro-HGF has the amino acid sequence shown in SEQ ID NO. 1.

[13] Active HGF characterized in that it is obtained by the production method according to any of [10] to [12].

Those skilled in the art shall recognize that an invention of any combination of one or more characteristics of the present invention described above is also encompassed by the scope of the present invention.

Effects of the Invention

According to the present invention, a method for producing active HGFA and active HGF without using animal serum is provided.

In the method for producing the active HGF of the present invention, since there is no need to use any animal serum in the production process thereof, a composition comprising the active HGF obtained by the aforementioned production method does not comprise animal serum-derived component and can be extremely safely applied to human.

BRIEF DESCRIPTION OF THE DRAWINGS

FIG. 1 shows that an HGFA culture supernatant prepared by activation of a pro-HGFA culture supernatant activates pro-HGF in a culture supernatant derived from CHO cells comprising pro-HGF.

FIG. 2 shows the verification result employing design of experiments (DoE) regarding conditions under which the pro-HGFA culture supernatant is activated.

FIG. 3 shows SDS-PAGE after chromatographic purification that employs a multimodal anion exchanger Capto Adhere as the chromatography support and 20 mM Tris-hydrochloride buffer (pH 8.0) comprising 0.25 M arginine and 0.7 M arginine as the eluent.

DESCRIPTION OF EMBODIMENTS

Figure 4:
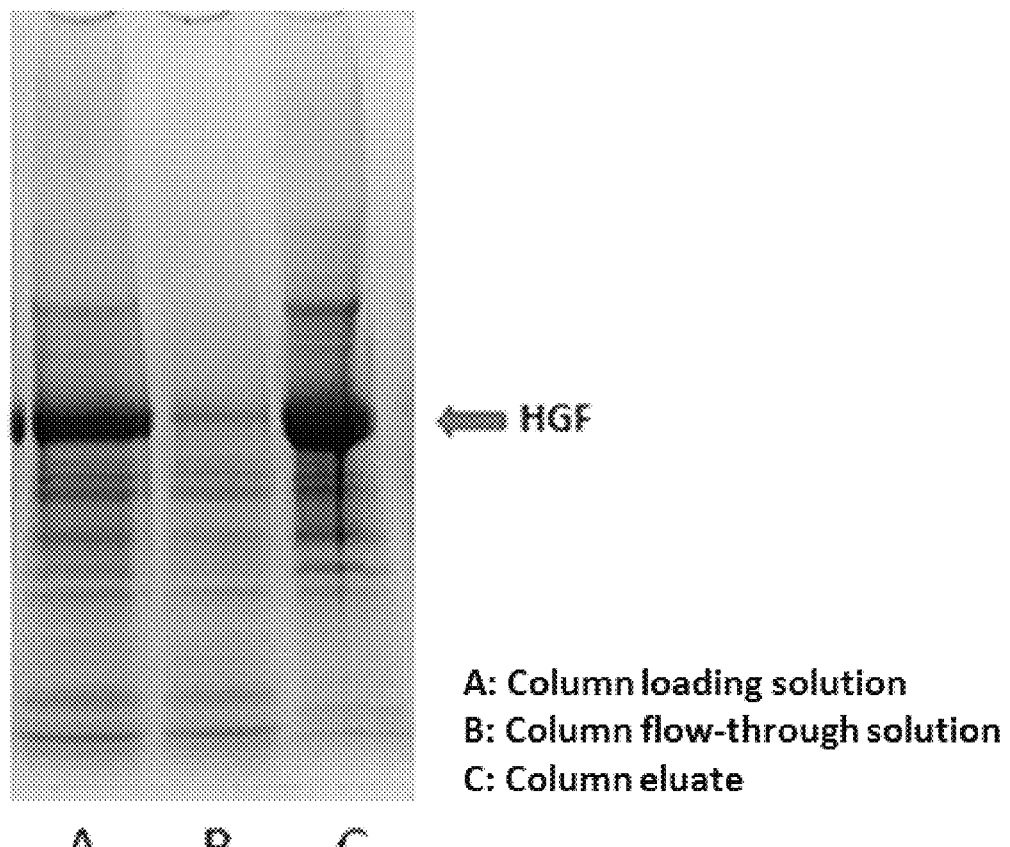
FIG. 4 shows SDS-PAGE after chromatographic purification that employs a multimodal anion exchanger Capto Adhere as the chromatography support and 20 mM Tris-hydrochloride buffer (pH 8.0) comprising 1 M arginine as the eluent.

Reference herein to "active hepatocyte growth factor (active HGF)," unless otherwise explicitly shown, is construed as referring to the double-stranded activated HGF form, and is used in discrimination with inactive hepatocyte growth factor (pro-HGF) which is the single-stranded inactive form thereof.

In the present invention, HGF may comprise HGF derived from humans, mice, rats, rabbits, or other animals. In the present invention, HGF is preferably HGF derived from humans.

In the present invention, human HGF (hHGF) includes a polypeptide having the amino acid sequence shown in SEQ ID NO. 1 or a variant thereof. A variant of the polypeptide having the amino acid sequence shown in SEQ ID NO. 1 includes a polypeptide having an amino acid sequence having addition, deletion, or substitution of one or multiple amino acids to the amino acid sequence shown in SEQ ID NO. 1, as well as having HGF activity similar to or more than the polypeptide having the amino acid sequence shown in SEQ ID NO. 1 or which may be activated to have the activity. "Multiple" as used herein is 2-150, more preferably 2-80, more preferably 2-70, more preferably 2-60, more preferably 2-50, more preferably 2-40, more preferably 2-30, more preferably 2-20, more preferably 2-10, or more preferably 2-5.

A variant of the polypeptide having the amino acid sequence shown in SEQ ID NO. 1 also includes a polypeptide having an amino acid sequence showing at least 80%, more preferably at least 85%, and more preferably at least 90%, 91%, 92%, 93%, 94%, 95%, 96%, 97%, 98%, or 99% sequence identity with the amino acid sequence shown in SEQ ID NO. 1, as well as having HGF activity similar to or more than the polypeptide having the amino acid sequence shown in SEQ ID NO. 1 or which may be activated to have the activity.

A variant of the polypeptide having the amino acid sequence shown in SEQ ID NO. 1 also includes a polypeptide having the amino acid sequence encoded by a polynucleotide that hybridizes under stringent condition to a polynucleotide encoding the amino acid sequence shown in SEQ ID NO. 1, as well as having HGF activity similar to or more than the polypeptide having the amino acid sequence shown in SEQ ID NO. 1 or which may be activated to have the activity.

In the present invention, a "stringent condition" can include those where in the post hybridization washing, hybridization is achieved with washing at for example a condition of "2×SSC, 0.1% SDS, 50° C.," a condition of "2×SSC, 0.1% SDS, 42° C.," or a condition of "1×SSC, 0.1% SDS, 37° C.," and a more stringent condition can include those where hybridization is achieved with washing at for example conditions of "2×SSC, 0.1% SDS, 65° C.," "0.5×SSC, 0.1% SDS, 42° C.," "0.2×SSC, 0.1% SDS, 65° C.," or "0.1×SSC, 0.1% SDS, 65° C." (1×SSC is 150 mM sodium chloride, 15 mM sodium citrate, pH 7.0). More particularly, as a method that employs Rapid-hyb buffer (Amersham Life Science), it is conceivable to perform prehybridization at 68° C. for 30 minutes or more, after which a probe is added and retained at 68° C. for 1 hour or more to allow formation of hybrids, and then to perform three washes in 2×SSC and 0.1% SDS at room temperature for 20 minutes, three washes in 1×SSC and 0.1% SDS at 37° C. for 20 minutes, and finally two washes in 1×SSC and 0.1% SDS at 50° C. for 20 minutes. More preferably, using a solution, for example, comprising 5×SSC, 7% (W/V) SDS, 100 µg/mL denatured salmon sperm DNA, and 5×Denhardt's solution (1×Denhardt's solution comprises 0.2% polyvinylpyrrolidone, 0.2% bovine serum albumin, and 0.2% Ficoll) as prehybridization and hybridization solutions, prehybridization is performed at 65° C. for 30 minutes to 1 hour and hybridization is performed at the same temperature overnight (6-8 hours). In addition, it is also possible to perform for example prehybridization in Expresshyb Hybridization Solution (CLONTECH) at 55° C. for 30 minutes or more, add a labeled probe and incubate at 37-55° C. for 1 hour or more, and three washes in 2×SSC and 0.1% SDS at room temperature for 20 minutes and then one washing in 1×SSC and 0.1% SDS at 37° C. for 20 minutes. Here, a more stringent condition can be achieved for example by raising the temperature for prehybridization, hybridization, or second washing. For example, the temperature for prehybridization and hybridization can be 60° C., or 65° C. or 68° C. for a further stringent condition. Those skilled in the art will be able to set conditions for obtaining isoforms, allelic variants, and corresponding genes derived from other organism species for the gene of the present invention by factoring in various conditions such as other probe concentration, probe length, and reaction time in addition to conditions such as salt concentration of such a buffer and temperature. For a detailed protocol of the hybridization method, reference can be made to "Molecular Cloning, A Laboratory Manual 2nd ed." (Cold Spring Harbor Press (1989); in particular Section 9.47-9.58), "Current Protocols in Molecular Biology" (John Wiley & Sons (1987-1997); in particular Section 6.3-6.4), "DNA Cloning 1: Core Techniques, A Practical Approach 2nd ed." (Oxford University (1995); in particular Section 2.10 for conditions), and the like.

Reference herein to "active hepatocyte growth factor activator (active HGFA)," unless otherwise explicitly shown, is construed as referring to activated HGFA, and is used in discrimination with inactive hepatocyte growth factor activator (pro-HGFA) which is the inactive form thereof.

In the present invention, HGFA may include HGFA derived from human, mouse, rat, rabbit, or other animals. In the present invention, HGFA is preferably HGFA derived from humans.

In the present invention, human HGFA includes a polypeptide having an amino acid sequence shown in SEQ ID NO. 2 or a variant thereof. The variant of the polypeptide having the amino acid sequence shown in SEQ ID NO. 2 includes a polypeptide having an amino acid sequence having addition, deletion, or substitution of one or multiple amino acids to the amino acid sequence shown in SEQ ID NO. 2, as well as having HGF activity similar to or more than the polypeptide having the amino acid sequence shown in SEQ ID NO. 2 or which may be activated to have the activity. "Multiple" as used herein is 2-150, more preferably 2-80, more preferably 2-70, more preferably 2-60, more preferably 2-50, more preferably 2-40, more preferably 2-30, more preferably 2-20, more preferably 2-10, or more preferably 2-5.

The variant of the polypeptide having the amino acid sequence shown in SEQ ID NO. 2 also includes a polypeptide having an amino acid sequence showing at least 80%, more preferably at least 85%, and more preferably at least 90%, 91%, 92%, 93%, 94%, 95%, 96%, 97%, 98%, or 99% sequence identity with the amino acid sequence shown in SEQ ID NO. 2, as well as having HGFA activity similar to or more than the polypeptide having the amino acid sequence shown in SEQ ID NO. 2 or which may be activated to have the activity.

The variant of the polypeptide having the amino acid sequence shown in SEQ ID NO. 2 also includes a polypeptide having the amino acid sequence encoded by a polynucleotide that hybridizes under stringent condition to a polynucleotide encoding the amino acid sequence shown in SEQ ID NO. 2, as well as having HGF activity similar to or more than the polypeptide having the amino acid sequence shown in SEQ ID NO. 2 or which may be activated to have the activity.

The present invention is described in detail below.

In one aspect, the present invention relates to a method for producing active HGFA without using animal serum. Specifically, the method for producing the active HGFA of the present invention is a method for producing active HGFA by subjecting a culture supernatant comprising pro-HGFA recombinantly expressed in mammalian cells to a given treatment to thereby allow conversion into active HGFA. Since animal serum is not used in the conversion into active HGFA, according to the present method, the pro-HGFA obtained or a composition comprising the same has significantly lower possibility of inviting the risk of being contaminated with infective materials such as virus derived from cells of other animal species or other individuals, and can be employed for various purposes as a highly safe biological material.

Specifically, in one embodiment, the method for producing the active HGFA of the present invention is characterized in that it comprises the following steps:

Step 1:

a step of obtaining a culture supernatant comprising pro-HGFA by culturing mammalian cells expressing pro-HGFA in a medium without serum, and Step 2:

a step of adjusting the culture supernatant comprising pro-HGFA obtained in the above step to weakly acidic to convert pro-HGFA into active HGFA.

In another embodiment, the HGFA production method of the present invention is characterized in that it comprises a step of adjusting the culture supernatant comprising pro-HGFA to weakly acidic to convert pro-HGFA into active HGFA, wherein said culture supernatant is a culture supernatant obtained by culturing mammalian cells expressing pro-HGFA in a medium without serum.

Weak acidification of the culture supernatant is a treatment for converting pro-HGFA into active HGFA. Since conversion from pro-HGFA into active HGFA occurs by weak acidification alone without externally adding enzymes etc. to the culture supernatant, mammalian cell-derived components are thought to be involved in the conversion from pro-HGFA into active HGFA, and weak acidification is a means for activating said mammalian cell-derived components. Weak acidification may be performed by means well-known to those skilled in the art, such as adding for example an acidic solution (inorganic acids such as hydrochloric acid, sulfuric acid, and phosphoric acid, or organic acids such as acetic acid, succinic acid, and citric acid) at an appropriate concentration. In one embodiment of the present invention, "weakly acidic" is a range of pH 4.0-6.0, preferably 5.0-6.0, and more preferably 5.3-5.6, for example pH 5.5.

In the present invention, a "culture supernatant comprising pro-HGFA" (also referred to herein as a "pro-HGFA culture supernatant") is a fraction comprising pro-HGFA that is obtained by cell culturing mammalian cells expressing pro-HGFA, which can be obtained from a cell culture of said mammalian cells by those skilled in the art according to conventional means. For example, the pro-HGFA culture supernatant may be a fraction where residues are removed from a cell culture of said mammalian cells by a means such as centrifugation.

In the present invention, the culture supernatant may be any fraction prepared by applying any treatment to the culture supernatant to an extent that the biological activity of pro-HGFA is not lost. Accordingly, in the present invention, the culture supernatant includes, but is not limited to, the culture supernatant per se, and a dilution, a concentrate or a partially purified product of the culture supernatant.

In a preferred embodiment of the present invention, the "step of converting pro-HGFA into active HGFA" further comprises adding sulfated polysaccharides to said culture supernatant. By adding sulfated polysaccharides, the conversion from pro-HGFA into active HGFA can be performed more efficiently. The timing for adding sulfated polysaccharides may be at any time point of before weak acidification of said culture supernatant, simultaneously with weak acidification, or after weak acidification. Moreover, the amount of sulfated polysaccharides added may vary depending on e.g. the type of sulfated polysaccharides used, and may be added at an amount of 0.01-50 mg, more preferably 0.1-20 mg, for example 1 mg per 1 mL of said pro-HGFA culture supernatant.

Sulfated polysaccharides that can be used for the method for producing the active HGFA of the present invention can include, but are not limited to, peparin, dextran sulfate, chondroitin sulfate, fucoidan, and salts thereof. In a preferred embodiment of the present invention, dextran sulfate is used.

In a preferred embodiment of the present invention, the "step of converting pro-HGFA into active HGFA" is performed at a temperature of 15-40° C., preferably 20-37° C., for example 25° C. By employing said temperature range, the conversion of pro-HGFA into active HGFA can be made more efficient.

In the method for producing the active HGFA of the present invention, the "step of converting pro-HGFA into active HGFA" is performed for a length of time sufficient to recognize the desired HGFA activity after weak acidification. Such a length of time may vary depending on pH, the presence or absence of sulfated polysaccharide used in combination, and temperature condition etc., and can be 1-15 hours, for example 6-8 hours after weak acidification.

In one embodiment of the present invention, the pro-HGFA culture supernatant is a culture supernatant that is obtained after a decline in the survival rate of mammalian cells in culture. Along with the decline in the survival rate of the mammalian cells, the animal cell-derived components involved in the conversion from pro-HGFA into active HGFA are eluted out from dead cells, and can be sufficiently collected in the pro-HGFA culture supernatant. The "decline in the survival rate of mammalian cells in culture" herein refers to the decline in the survival rate of the mammalian cells after proliferation to maximum cell density. In the present invention, the survival rate of mammalian cells in the pro-HGFA culture supernatant is preferably 95% or less, more preferably 80% or less, for example 70%.

Since an enzyme derived from host cell lysosome is thought to be involved in the activation from pro-HGFA to active HGFA, an enzyme derived from lysosome may be added to apply treatment.

Mammalian cells that can be used in the method for producing the active HGFA of the present invention can include, but are not limited to, Chinese hamster ovary (CHO) cells, HeLa cells, HEK cells (including HEK 293 cells), COS cells, NS0 mouse myeloma cells, Sp2/0 mouse myeloma cells, and the like. In a preferred embodiment of the present invention, CHO cells are used as mammalian cells expressing pro-HGFA.

The present invention also relates to a composition comprising active HGFA or active HGFA produced by the method for producing the active HGFA of the present invention. Since the composition comprising active HGFA or active HGFA of the present invention can be produced without using animal serum from recombinantly expressed pro-HGFA without using animal serum, it can be used as a highly safe biological material e.g. for the method for producing the active HGF described below.

In another aspect, the present invention relates to a method for producing active HGF. The method for producing the active HGF of the present invention comprises allowing active HGFA obtained by the method for producing the active HGFA of the present invention to act on a culture supernatant comprising pro-HGF recombinantly expressed in a medium similarly without serum to convert pro-HGF into active HGF. According to this method, since active HGF can be produced without employing animal serum in all of the steps including obtaining active HGFA employed for conversion into active HGF, the active HGF obtained or a composition comprising the same can be used as a highly safe pharmaceutical material that eliminates the risk of being contaminated with infective materials such as virus.

Specifically, in one embodiment, the method for producing the active HGF of the present invention is characterized in that it comprises a step of allowing active HGFA to act on a culture supernatant comprising pro-HGF to convert said pro-HGF into active HGF, wherein said culture supernatant comprising pro-HGF is a culture supernatant obtained by culturing cells expressing pro-HGF in a medium without serum, and said active HGFA is produced by the above method for producing the active HGFA of the present invention.

Moreover, in another embodiment, the method for producing the active HGF of the present invention is characterized in that it comprises the following steps:

Step A:

a step of adjusting the culture supernatant comprising pro-HGFA to weakly acidic to convert pro-HGFA into active HGFA, wherein said culture supernatant is a culture supernatant obtained by culturing mammalian cells expressing pro-HGFA in a medium without serum, Step B:

a step of obtaining a culture supernatant comprising pro-HGF by culturing cells expressing pro-HGF in a medium without serum, Step C:

a step of allowing the active HGFA obtained in said step A to act on the culture supernatant comprising pro-HGF obtained in said step B to convert said pro-HGF into active HGF.

In the present invention, a "culture supernatant comprising pro-HGF" is a fraction comprising pro-HGF that is obtained by culturing cells expressing pro-HGF, and those skilled in the art can obtain the same from a culture of said cells according to conventional means. For example, a culture supernatant comprising pro-HGF may be a fraction where residues are removed from a culture of said cells by a means such as centrifugation.

In the method for producing the active HGF of the present invention, a culture supernatant obtained by culturing mammalian cells expressing pro-HGFA in a medium without serum may be employed as it is, or a dilution, a concentrate, or a partially or completely purified product of the aforementioned culture supernatant may be employed as the active HGFA that is allowed to act on the "culture supernatant comprising pro-HGF."

In the present invention, a mammalian cell expressing pro-HGFA can be obtained by, but not limited to, creating a vector comprising a nucleic acid encoding pro-HGFA, and introducing this into a host cell mammalian cell to allow transformation. Similarly, a cell expressing pro-HGF can be obtained by creating a vector comprising a nucleic acid encoding pro-HGF, and introducing this into a host cell to allow transformation.

A gene expression vector etc. can be used as the above-described vector. A "gene expression vector" is a vector which has the function to express the base sequence that the nucleic acid of interest has, and may include a promoter sequence, an enhancer sequence, a repressor sequence, an insulator sequence, and the like for controlling the expression of said base sequence. These sequences are not particularly limited as long as they function in the host cell.

The means to create the vector comprising the nucleic acid of interest is well-known to those skilled in the art, and those skilled in the art can suitably select an appropriate method. For example, such a means can include, but is not limited to, a ligase reaction that utilizes a restriction enzyme site and the like (Current Protocols in Molecular Biology, John Wiley & Sons (1987) Section 11.4-11.11; Molecular Cloning, A Laboratory Manual 2nd ed., Cold Spring Harbor Press (1989) Section 5.61-5.63).

The cells expressing pro-HGF are not particularly limited as long as they can express pro-HGF, and include, for example, insect cells, eukaryotic cells, mammalian cells. Preferably, in terms of efficiently expressing a nucleic acid encoding pro-HGF derived from human, mammalian cells, e.g., CHO cells, HEK cells (including HEK 293 cells), HeLa cells, NS0 cells, or SP2/0 mouse myeloma cells are used. In a preferred embodiment of the invention, CHO cells are used as the mammalian cell expressing pro-HGF.

The means for introducing the above vector into a host cell is well-known, and those skilled in the art can suitably select an appropriate method. Examples can include, but are not limited to, for introduction of a vector into a host cell, electroporation method (Chu et al. (1987) Nucleic Acids Res. 15: 1311-26), cationic liposome method, electrical pulse perforation method (Current Protocols in Molecular Biology, John Wiley & Sons (1987) Section 9.1-9.9), direct inject method using a capillary glass tube, microinjection method, lipofection (Derijard (1994) Cell 7: 1025-37; Lamb (1993) Nature Genetics 5: 22-30; Rabindran et al. (1993) Science 259: 230-4), lipofectamine method (Thermo Fisher Scientific), calcium phosphate method (Chen and Okayama (1987) Mol. Cell. Biol. 7: 2745-52), DEAE dextran method (Lopata et al. (1984) Nucleic Acids Res. 12: 5707-17; Sussman and Milman (1985) Mol. Cell. Biol. 4: 1642-3), FreeStyle MAX Reagent (Thermo Fisher Scientific), and the like.

In regards to the serum-free medium used for culturing cells expressing pro-HGFA and cells expressing pro-HGF, those skilled in the art can suitably select an appropriate composition depending on the type of host cell etc. used. Moreover, other culture conditions can also be suitably selected by those skilled in the art, and for example, but not limited to, the culture temperature can be suitably selected from between 35.5-37.5° C., and the culture period can be selected from between 5-20 days. For pro-HGFA, the culture period may be set according to the target survival rate. The carbon dioxide concentration during culture can be 5% $CO_2$ in accordance to the general protocol.

In one embodiment, the method for producing the active HGF of the present invention is characterized in that followed by said step, it further comprises a step of purifying active HGF. This step may include purification of pro-HGF that may remain in the preparation comprising active HGF.

The purification method that may be used in the present invention is not particularly limited as long as it enables purification without losing the physiologic activity of the protein. In particular, it is preferred to use chromatographic purification employing a mixed mode support in the present invention.

Mixed mode support is also referred to as mixture mode support, and is a chromatography support in which ligands of modes with two or more types of properties are bound into one support. In particular, in the present invention, for the purification of active HGF, active HGF can be efficiently purified by chromatographic purification employing a mixed mode support having characteristics of hydrophobicity and ion exchange support.

Examples of a "mixed mode support having characteristics of hydrophobicity and ion exchange support" that may be used in the method of the present invention can include, but are not limited to, Capto adhere, Capto MMC, HEA HyperCel, PPA HyperCel, MEP HyperCel, TOYOPEARL MX-Trp-650M, and the like.

Chromatographic purification employing said mixed mode support can be performed by adsorbing active HGF in the column loading solution to said mixed mode support, and then washing with a buffer to remove impurities, followed by elution. The buffer for removing impurities can be set based on the pH, electric conductivity, buffer component, salt concentration, or additives that maintain the adsorption between the protein which is the target for purification and the support while reducing the affinity between impurities and the support.

Examples of the column loading solution and buffer used include, but are not limited to, phosphate salts, citrate salts, acetate salts, succinate salts, maleate salts, borate salts, Tris (base), HEPES, MES, PIPES, MOPS, TES, or Tricine and the like.

The column loading solution and buffer used can comprise amino acids. Examples of such amino acids can include, but are not limited to, glycine, alanine, arginine, serine, threonine, glutamic acid, aspartic acid, histidine, derivatives thereof, and the like.

In the present invention, a column loading solution that has suitable pH and salt concentration for adsorbing active HGF onto said mixed mode support can be used. Such a pH range is pH 6.0-10.0, more preferably pH 7.0-9.0, for example pH 8.0. Moreover, such a salt concentration is 0.01-5 M, preferably 0.1-2 M, for example 1 M. The above salt concentration can be prepared by employing for example 0.001 M-4 M sodium chloride, potassium chloride, calcium chloride, sodium citrate, sodium sulfate, ammonium sulfate, or a combination thereof.

In the present invention, elution of active HGF can be performed by employing a buffer that will reduce the affinity between said mixed mode support and active HGF. Such a buffer includes a buffer comprising at least 0.1 M arginine, more preferably at least 0.3 M arginine, further preferably at least 0.4 M arginine, for example 0.7 M arginine. Moreover, in combination with or instead of arginine, a buffer comprising magnesium ion ($Mg^{2+}$) can also be employed. Alternatively, elution of active HGF may also be performed by a stepwise method that reduces pH stepwise to elute active HGF.

In one embodiment of the present invention, said purification may further comprise, after purification by a mixture mode support comprising an ion exchange group and a hydrophobic interaction group, purification by single or multiple additional chromatographies. This will enable active HGF to be obtained at higher purity. Such a chromatographic purification includes, but is not limited to, for example chromatographic purification that employs a mixed mode support, an anion exchange support, a cation exchange support, a hydrophobic interaction support, a size exclusion support, a gel filtration support, a reverse phase support, a hydroxyapatite support, a fluoroapatite support, a sulfated cellulose support, or a sulfated agarose support and the like.

Note that the terms used herein are to be employed to describe particular embodiments and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

Terms such as first and second are sometimes employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The present invention will now be more specifically described by Examples. However, the present invention can be embodied by various embodiments, and shall not be construed as being limited to the Examples described herein.

EXAMPLES

The present invention will be specifically described below by showing Examples, but the present invention is not to be limited by the Examples.

Example 1

CHO cells that recombinantly express full length pro-HGFA were thawed in EX-CELL custom design medium (from SAFC) in a T75 flask (from Corning, 430421), expansion culture was performed in a 250 mL shaker flask (from Corning, 431144), and then cultured for 10 days in a 7 L culture tank (from ABLE/Biott, BCP-07) at 121 rpm set at 36.5° C. The survival rate of the cells at Day 10 of culturing was 47.1%. After completion of culture, cells were removed by centrifugation and microfiltered through a 0.2 μm filter (from Sartorius, 5445307H7—00), and the pro-HGFA supernatant collected was stored under refrigeration until use.

50 mL of pro-HGFA culture supernatant obtained similarly as above was placed in a 100 mL glass beaker, 5 mL, which is 1/10 volume of the supernatant, of 10 g/L aqueous solution of dextran sodium sulfate (Mw. 500,000) was added, and then pH was adjusted to 5.3 with 2 M hydrochloric acid. After the pH adjustment, it was subjected to filtration with a 0.2 μm filter, and then placed in a 250 mL shaker flask. Five percent carbon dioxide was blown in for 60 seconds, and then reaction was performed at room temperature with stirring speed set at 80 rpm for 6 hours. The activation reaction was progressed at around pH 5.5. Sampling was performed after 6 hours of reaction, and HGFA activity was measured with synthetic peptide as the substrate. The synthetic substrate H-D-Val-Leu-Arg-pNA.2AcOH (from Bachem, L-1885) was dissolved in 50 mM Tris-HCl—0.15 M sodium chloride—10 mM calcium chloride buffer (pH 7.5) comprising 0.25% BSA, and adjusted to 2 mM. This was applied at 100 μL/well in the necessary number of wells in a 96-well plate, and 10 μL each of the HGFA culture supernatant which had been subjected to activation treatment, positive control, and untreated pro-HGFA culture supernatant were added. As the positive control, HGFA culture supernatant which had been activated in advance and was confirmed to be capable of sufficiently activating pro-HGF was employed. The plate was shielded from light with an aluminum foil, and incubated at 37° C. for 1 hour. Absorbance was read with a plate reader from TECAN (405 nm), and HGFA activity value was caluculated by subtracting an absorbance of untreated pro-HGFA culture supernatant from the original absorbance. As a result, it was confirmed that the activity value of the HGFA sample after activation showed 0.577, which is comparable to the activity value of the positive control. It is thought that pro-HGFA is activated by the action of an enzyme derived from the host CHO cell since any enzymes and the like were not externally added to this reaction solution. Moreover, when 1 M Tris was added to the solution after 7.6 hours of reaction to adjust pH to 7.0 and then the solution was stored under refrigeration for 2 days to examine the change in HGFA activity value, a large decline in the activity value was not seen with the activity value immediately after neutralization at 0.653, Day 1 of refrigeration at 0.667, and Day 2 of refrigeration at 0.679, showing stability for 2 days after activation (Table 1).

TABLE 1

HGFA Activity Value After Activation Treatment

|  | Sample | A405 | HGFA Activity Value |
|---|---|---|---|
| Measurement 1 | Pro-HGFA culture supernatant | 0.100 | — |
|  | 6 hours after activation | 0.677 | 0.577 |
|  | Positive-control | 0.709 | 0.609 |
| Measurement 2 | Pro-HGFA culture supernatant | 0.110 | — |
|  | 7.6 hours after activation (before neutralization) | 0.803 | 0.693 |
|  | 7.6 hours after activation (after neutralization) | 0.763 | 0.653 |
|  | Day 1 of refrigerated storage after neutralization | 0.777 | 0.667 |
|  | Day 2 of refrigerated storage after neutralization | 0.789 | 0.679 |
|  | Positive-control | 0.714 | 0.604 |

CHO cells that recombinantly express pro-HGF were thawed in EX-CELL custom design medium in a T75 flask, expansion culture was performed in a 250 mL shaker flask and a 7 L culture tank, and this was then cultured for 9 days in a 20 L culture tank at 144 rpm set at 36.5° C. The survival rate at Day 9 of culturing was 90.6%. After filtration to remove cells, 19.14 kg of pro-HGF culture supernatant that had been microfiltered through a 0.2 μm filter (from Sartorius, 5445307H9—00) was charged into a 30 L culture tank. To this, 0.96 kg, which is 1/20 volume of the HGF supernatant, of the HGFA culture supernatant that had been activated and returned to pH 7.0 and stored under refrigeration for 2 days was added and reacted with stirring at 30 rpm at 25° C. Note that the activated HGFA culture supernatant charged was that which had an activity value comparable to the positive control in HGFA activity measurement. Sampling was performed after about 20 hours of reaction, and the activation state of pro-HGF was confirmed with SDS-PAGE employing 5-20% polyacrylamide gel (from DRC, NXV-271HP). A band of single strand was seen under a non-reductive condition, and under a reductive condition after activation the single strand substance had disappeared and separated into α and β chains, and thus sufficient activation of pro-HGF was confirmed (FIG. 1).

Example 2

Using design of experiments (DoE), the validity of pro-HGFA activation parameters described in Example 1 which are pH (5.3-5.5) and reaction temperature (room temperature) was tested. Experiment conditions were set with central composite design using JMP software (from SAS Institute), and a solution for pro-HGFA activation treatment was prepared similarly to the method described in Example 1. Note that pH was adjusted to three conditions of pH 5.0, 5.5, and 6.0 with 2 M hydrochloric acid. 100 μl each were placed in 1.5 mL tubes and reacted by still standing at 20° C., 28.5° C. and 37° C. Sampling was performed after 3, 6, 9, and 15 hours of reaction, and HGFA activity measured with synthetic peptide as the substrate. HGFA activity value is obtained by subtracting the value (A405) of untreated pro-HGFA culture supernatant. A response surface plot was created by statistical analysis from the HGFA activity values obtained from a total of 27 conditions, and the range having an activity value of 0.4 or more was shown in white. From this result, it was found that the condition that gives the highest HGFA activity value is pH 5.4 and a reaction temperature of 26.1° C., and that HGFA activity value can be obtained in a wide range (FIG. 2).

Example 3

2 mL of multimodal anion exchanger Capto Adhere (from GE Healthcare, 28-4058-44) was equilibrated in advance with 20 mM Tris-hydrochloride buffer (pH 8.0) comprising 2 M sodium chloride. To 32 mL of culture supernatant comprising active HGF, sodium chloride was added to obtain 1 M. This culture supernatant was loaded onto the column at a flow rate of 2 mL/min and the flow-through solution was collected. After loading was complete, 20 mM Tris-hydrochloride buffer (pH 8.0) comprising 2 M sodium chloride was flowed at an amount corresponding to 3 times of the column volume to wash, and the eluate was collected. After washing was complete, 20 mM Tris-hydrochloride buffer (pH 8.0) comprising 0.25 M arginine was flowed at an amount corresponding to 3 times of the column volume to wash and the eluate was collected. Next, an operation to flow 20 mM Tris-hydrochloride buffer (pH 8.0) comprising 0.7 M arginine at an amount corresponding to 1 column volume to collect the eluate was repeated 5 times. Finally, 20 mM Tris-hydrochloride buffer (pH 8.0) comprising 1.0 M arginine was flowed at an amount corresponding to 3 times of the column volume to collect the eluate. FIG. 3 shows the result of performing SDS-PAGE under a non-reductive condition with the solutions collected in this process. The gel for SDS-PAGE employed was XV-PANTERA (NXV-271HP) from DRC, and the molecular weight marker employed was Precision Plus Protein All Blue Standards (161-0373) from BIORAD. The samples were subjected to SDS-PAGE analysis after performing 10 minutes of heat treatment in Laemmli's sample buffer at 60° C. Electrophoresis was performed under a constant voltage of 150 V, and the gel was stained when the electrophoresis was complete with PAGE Blue83 from COSMO BIO to confirm the separated proteins. When comparing the column loading solution and the flow-through solution, the HGF band of molecular weight of around 75,000 was decreased in the flow-through solution, showing that it was adsorbed onto the support. HGF was not eluted by flowing through 20 mM Tris-hydrochloride buffer (pH 8.0) comprising 2 M sodium chloride. A component comprising much impurity was eluted in subsequent washing with 20 mM Tris-hydrochloride buffer (pH 8.0) comprising 0.25 M arginine. Active HGF was then eluted by flowing through 20 mM Tris-hydrochloride buffer (pH 8.0) comprising 0.7 M arginine.

Example 4

1 mL of multimodal anion exchanger Capto Adhere (from GE Healthcare, 28-4058-44) was equilibrated in advance with 20 mM Tris-hydrochloride buffer (pH 8.0) comprising 2 M sodium chloride. To 8 mL of culture supernatant comprising active HGF was added an equal amount of 20 mM Tris-hydrochloride buffer (pH 8.0) comprising 2 M sodium chloride to obtain 1 M. This culture supernatant was loaded onto the column and the flow-through solution was collected. After loading was complete, 20 mM Tris-hydrochloride buffer (pH 8.0) comprising 2 M sodium chloride was flowed at an amount corresponding to 3 times of the column volume to wash, and the eluate was collected. An amount corresponding to 5 times of the column volume of 20 mM Tris-hydrochloride buffer (pH 8.0) comprising 1 M arginine was flowed, and the eluate was collected. FIG. 4 shows the result of performing SDS-PAGE under a non-reductive condition with the solutions collected in this process. The gel for SDS-PAGE employed was XV-PANTERA (NXV-271HP) from DRC, and the molecular weight marker employed was Precision Plus Protein All Blue Standards (161-0373) from BIORAD. The samples were subjected to SDS-PAGE analysis after performing 10 minutes of heat treatment in Laemmli's sample buffer at 60° C. Electrophoresis was performed under a constant voltage of 150 V, and the gel was stained when the electrophoresis was complete with PAGE Blue83 from COSMO BIO to confirm the separated proteins. When comparing the column loading solution and the flow-through solution, HGF band was decreased in the flow-through solution, showing that it was adsorbed onto the support. HGF was not eluted by flowing through 20 mM Tris-hydrochloride buffer (pH 8.0) comprising 2 M sodium chloride. Active HGF was eluted with the subsequent elution with 20 mM Tris-hydrochloride buffer (pH 8.0) comprising 1 M arginine.

Example 5

To the culture supernatant comprising active HGF obtained in the method of Example 1 was added an equal amount of 40 mM Tris-hydrochloride buffer (pH 8.0) comprising 2 M sodium chloride, and then the pH was adjusted to 8.0. The above solution was loaded onto a Capto adhere (GE Healthcare, 17-5444-05) column equilibrated with 20 mM Tris-hydrochloride buffer (pH 8.0) comprising 2 M sodium chloride, and after loading was complete, washing with the buffer employed for equilibration was performed. The column was washed with 20 mM Tris-hydrochloride buffer (pH 8.0) comprising 0.25 M arginine hydrochloric acid, after which it was eluted with 20 mM Tris-hydrochloride buffer (pH 8.0) comprising 0.7 M arginine hydrochloric acid, and the fraction comprising HGF was collected.

The Capto adhere purification fraction was pooled, the solution diluted 7 times with 20 mM Tris-hydrochloride buffer (pH 7.5) comprising 0.012% polysorbate 80 was loaded onto a Capto Q (GE Healthcare, 17-5316-05) column equilibrated with 20 mM Tris-hydrochloride buffer (pH 7.5) comprising 0.012% polysorbate 80, and after loading was complete, washing with the buffer employed for equilibration was performed. The column flow-through solution and the wash solution were pooled as the Capto Q purification fraction.

The Capto Q purification fraction was loaded onto a UNOsphere S (Bio-Rad 156-0117) column equilibrated with 20 mM phosphate buffer (pH 7.5), and after loading was complete, this was washed with the buffer employed for equilibration. After completion of washing with the same solution, this was washed with 20 mM phosphate buffer (pH 7.5) comprising 0.4 M sodium chloride, and then the adsorbed HGF was eluted with 20 mM phosphate buffer (pH 7.5) comprising 0.6 M sodium chloride as the UNOsphere S purification fraction.

To the UNOsphere S purification fraction was added 20 mM phosphate buffer (pH 7.5) comprising 5 M sodium chloride to adjust the sodium chloride concentration of the solution to 3.3 M and the pH to 7.5. Phenyl Sepharose HP (GE Healthcare, 17-1082-04 column) was equilibrated with 20 mM phosphate buffer (pH 7.5) comprising 3.3 M sodium chloride, and then the above HGF solution was loaded. After loading was complete, the column was washed with the buffer employed for equilibration. The adsorbed HGF was eluted by a linear gradient of the equilibration buffer (A) and 20 mM phosphate buffer (pH 7.5) (B) (from 30 to 100% of B).

Example 6

Figure 5:
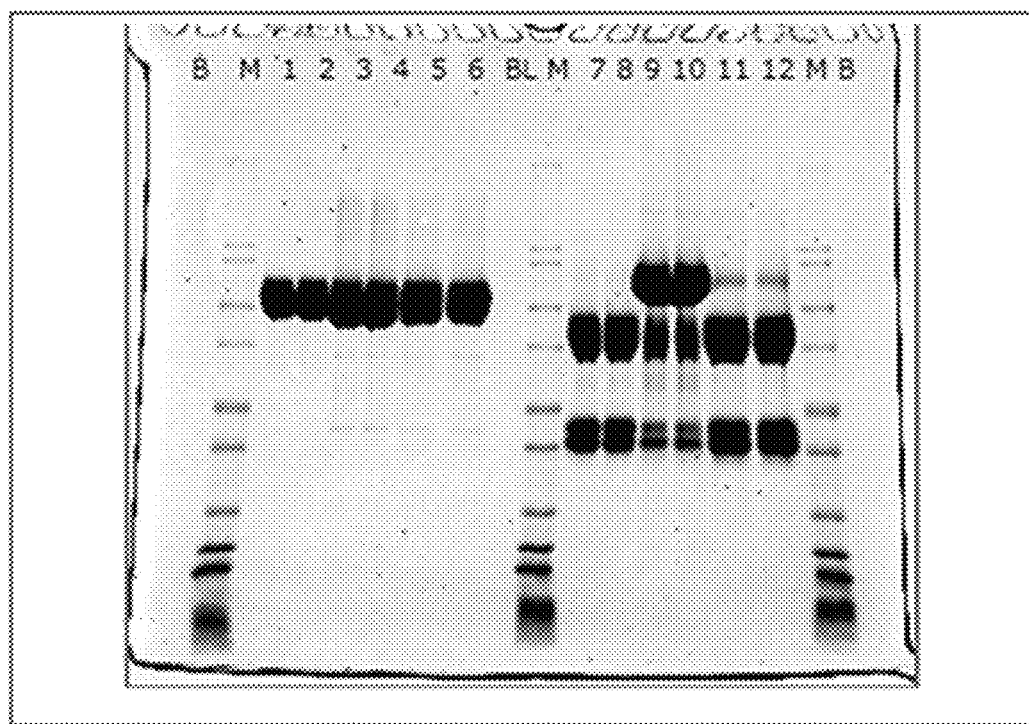
FIG. 5 shows non-reductive and reductive SDS-PAGE results of the purified product at each stage of purification where purification similar to Example 5 was performed with a culture supernatant comprising pro-HGF that is not activated by a HGFA culture supernatant.

For the culture supernatant comprising unactivated pro-HGF solution to which active HGFA was not added, Capto adherese purification, CaptoQ purification, UNOsphereS purification, and UF concentration buffer exchange were carried out similarly to Example 5. Non-reductive and reductive SDS-PAGE results of samples obtained in each step shown in FIG. 5 show that the unactivated pro-HGF is also purified in the present purification process.

Example 7

For the active HGF obtained in Example 5, cell proliferation activity in the presence of TGFβ-1 was measured. Using mink lung epithelial cell Mv 1 Lu (cell No.: JCRB9128), active HGF was added to cells of which the growth was inhibited in the presence of Transforming Growth Factor β-1 (TGFβ-1), and the active HGF proliferation activity thereof based on the antagonistic action on TGFβ-1 activity was detected to measure the titer (Journal of Immunological Methods, 258, 1-11, 2001).

Figure 6:
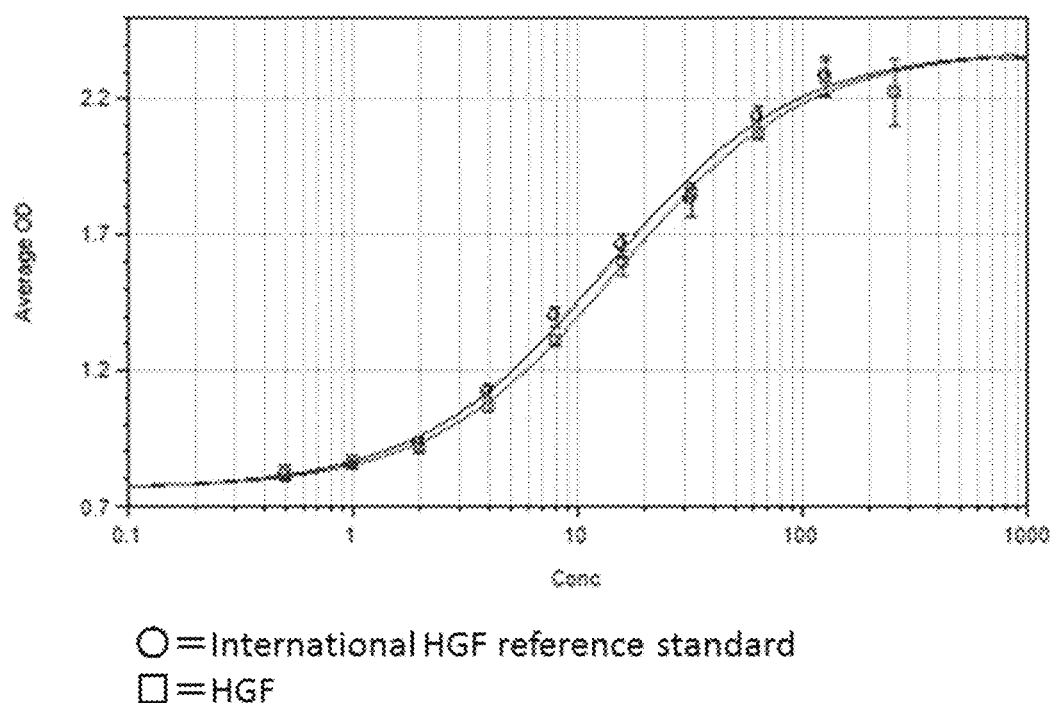
FIG. 6 shows the result of measuring cell proliferation activity in the presence of TGFβ for purified HGF obtained in Example 5.

In each well of a 96-well plate, 50 μL of TGFβ-1 (4 ng/mL), 50 μL each of International HGF reference standard (NIBSC code: 96/564) or HGF (0, 4, 8, 16, 32, 64, 128, 256, 512, and 1024 ng/mL), and 100 μL of mink lung epithelium cell suspension ($1 \times 10^5$ cells/mL) were added and cultured at 37° C., 5% $CO_2$ concentration for 3 days, and then viable cells were stained by Cell counting kit (DOJINDO LABORATORIES, Cat No. 343-07623). Using a microplate reader, sigmoid curves were obtained for each of International HGF reference standard and HGF from absorbance at 450 nm (FIG. 6). EC50 of International HGF reference standard and HGF was 13.4 and 15.4 ng/mL, respectively, and HGF obtained with the above production method had activity equivalent to that of the International HGF reference standard.

Sequence Listing
ESAP1601F sequence listing.txt

The invention claimed is:

1. A method for producing active hepatocyte growth factor activator (HGFA), comprising:
   a first step of obtaining a culture supernatant comprising inactive hepatocyte growth factor activator (pro-HGFA) by culturing mammalian cells expressing pro-HGFA in a cell culture medium without serum and then removing cells and cell residue from the cell culture medium, wherein said pro-HGFA comprises the amino acid sequence of SEQ ID NO:2, and
   a second step of adding an acidic solution to the culture supernatant comprising pro-HGFA obtained in the first step to adjust the culture supernatant to pH 4.0-6.0 and convert pro-HGFA into active HGFA.

2. The production method according to claim 1, wherein said second step further comprises adding sulfated polysaccharides to said culture supernatant.

3. A method for production of active hepatocyte growth factor (HGF), comprising:
   producing active hepatocyte growth factor activator (HGFA) according to the method of claim 2; and
   adding said active HGFA to a culture supernatant comprising inactive hepatocyte growth factor (pro-HGF) to convert said pro-HGF into active HGF,
   wherein said pro-HGF comprises the amino acid sequence of SEQ ID NO:1, and
   wherein said culture supernatant comprising pro-HGF is a culture supernatant obtained by culturing cells expressing pro-HGF in a cell culture medium without serum and then removing cells and cell residue from the cell culture medium.

4. The production method according to claim 3, wherein said cell culture medium for culturing cells expressing pro-HGF is a medium without any animal-derived components.

5. The production method according to claim 1, wherein said second step is performed at a temperature of 15-40° C.

6. A method for production of active hepatocyte growth factor (HGF), comprising:
   producing active hepatocyte growth factor activator (HGFA) according to the method of claim 5; and
   adding said active HGFA to a culture supernatant comprising inactive hepatocyte growth factor (pro-HGF) to convert said pro-HGF into active HGF,
   wherein said pro-HGF comprises the amino acid sequence of SEQ ID NO:1, and
   wherein said culture supernatant comprising pro-HGF is a culture supernatant obtained by culturing cells expressing pro-HGF in a cell culture medium without serum and then removing cells and cell residue from the cell culture medium.

7. The production method according to claim 6, wherein said cell culture medium for culturing cells expressing pro-HGF is a medium without any animal-derived components.

8. The production method according to claim 1, wherein said culture supernatant is obtained after a decline in the survival rate of the mammalian cells cultured in the cell culture medium.

9. A method for production of active hepatocyte growth factor (HGF), comprising:
   producing active hepatocyte growth factor activator (HGFA) according to the method of claim 8; and
   adding said active HGFA to a culture supernatant comprising inactive hepatocyte growth factor (pro-HGF) to convert said pro-HGF into active HGF,
   wherein said pro-HGF comprises the amino acid sequence of SEQ ID NO:1, and
   wherein said culture supernatant comprising pro-HGF is a culture supernatant obtained by culturing cells expressing pro-HGF in a cell culture medium without serum and then removing cells and cell residue from the cell culture medium.

10. The production method according to claim 9, wherein said cell culture medium for culturing cells expressing pro-HGF is a medium without any animal-derived components.

11. The production method according to claim 1, wherein said mammalian cells are Chinese hamster ovary (CHO) cells.

12. A method for production of active hepatocyte growth factor (HGF), comprising:
   producing active hepatocyte growth factor activator (HGFA) according to the method of claim 11; and
   adding said active HGFA to a culture supernatant comprising inactive hepatocyte growth factor (pro-HGF) to convert said pro-HGF into active HGF, wherein said pro-HGF comprises the amino acid sequence of SEQ ID NO:1, and wherein said culture supernatant comprising pro-HGF is a culture supernatant obtained by culturing cells expressing pro-HGF in a cell culture medium without serum and then removing cells and cell residue from the cell culture medium.

13. The production method according to claim 12, wherein said cell culture medium for culturing cells expressing pro-HGF is a medium without any animal-derived components.

14. The production method according to claim 1, wherein said method further comprises diluting or the culture supernatant obtained in the second step.

15. A method for production of active hepatocyte growth factor (HGF), comprising:

producing active hepatocyte growth factor activator (HGFA) according to the method of claim 14; and adding said active HGFA to a culture supernatant comprising inactive hepatocyte growth factor (pro-HGF) to convert said pro-HGF into active HGF, wherein said pro-HGF comprises the amino acid sequence of SEQ ID NO:1, and wherein said culture supernatant comprising pro-HGF is a culture supernatant obtained by culturing cells expressing pro-HGF in a cell culture medium without serum and then removing cells and cell residue from the cell culture medium.

16. The production method according to claim 15, wherein said cell culture medium for culturing cells expressing pro-HGF is a medium without any animal-derived components.

17. A method for production of active hepatocyte growth factor (HGF), comprising:

producing active hepatocyte growth factor activator (HGFA) according to the method of claim 1; and adding said active HGFA to a culture supernatant comprising inactive hepatocyte growth factor (pro-HGF) to convert said pro-HGF into active HGF, wherein said pro-HGF comprises the amino acid sequence of SEQ ID NO:1, and wherein said culture supernatant comprising pro-HGF is a culture supernatant obtained by culturing cells expressing pro-HGF in a cell culture medium without serum and then removing cells and cell residue from the cell culture medium.

18. The production method according to claim 17, wherein said cell culture medium for culturing cells expressing pro-HGF is a medium without any animal-derived components.

* * * * *

UNITED STATES PATENT AND TRADEMARK OFFICE
CERTIFICATE OF CORRECTION

| | |
|---|---|
| PATENT NO. | : 11,548,926 B2 |
| APPLICATION NO. | : 16/078568 |
| DATED | : January 10, 2023 |
| INVENTOR(S) | : Masashi Shimizu, Toshitaka Sato and Yoshihisa Arita |

It is certified that error appears in the above-identified patent and that said Letters Patent is hereby corrected as shown below:

In the Claims

In Column 25, Line 13, in Claim 14, after "or" insert -- concentrating --.

Signed and Sealed this
Twenty-first Day of March, 2023

Katherine Kelly Vidal
*Director of the United States Patent and Trademark Office*